US008299319B2

(12) United States Patent
Horvath et al.

(10) Patent No.: US 8,299,319 B2
(45) Date of Patent: Oct. 30, 2012

(54) PLANTS HAVING IMPROVED GROWTH CHARACTERISTICS AND A METHOD FOR MAKING THE SAME

(75) Inventors: Gabor Horvath, Szeged (HU); Sylvie Tarayre, Arpajon (FR); Eva Kondorosi, Bures sur Yvette (FR); Valerie Frankard, Rhodes-Saint-Genèse (BE)

(73) Assignees: CropDesign N.V. (BE); Centre National de la Recherche Scientifique (FR)

( * ) Notice: Subject to any disclaimer, the term of this patent is extended or adjusted under 35 U.S.C. 154(b) by 535 days.

(21) Appl. No.: 12/404,741
(22) Filed: Mar. 16, 2009
(65) Prior Publication Data

US 2009/0288228 A1  Nov. 19, 2009

Related U.S. Application Data

(63) Continuation of application No. 10/551,696, filed as application No. PCT/IB2004/000970 on Mar. 31, 2004, now abandoned.

(30) Foreign Application Priority Data

Mar. 31, 2003  (EP) .................................... 03290812

(51) Int. Cl.
*C12N 15/82* (2006.01)
*A01H 5/00* (2006.01)

(52) U.S. Cl. ...................... 800/290; 800/298; 435/320.1; 435/252.3

(58) Field of Classification Search ........................ None
See application file for complete search history.

(56) References Cited

U.S. PATENT DOCUMENTS

2007/0067875 A1   3/2007   Horvath et al.

FOREIGN PATENT DOCUMENTS

| WO | 99/64451 A | 12/1999 |
|----|------------|---------|
| WO | 00/56905 A | 9/2000 |
| WO | WO 03/000898 | 1/2003 |

OTHER PUBLICATIONS

Cebolla A. et al. The mitotic inhibitor ccs52 is required for endoreduplication and ploidy-dependent cell enlargement in plants. EMBO J. Aug. 16, 1999;18(16):4476-84.*
Norris S. et al. The intron of *Arabidopsis thaliana* polyubiquitin genes is conserved in location and is a quantitative determinant of chimeric gene expression. Plant Mol Biol. Mar. 1999;21(5):895-906.*
Binet M. et al. Structure and expression of sunflower ubiquitin genes. Plant Mol Biol. Sep. 1991;17(3):395-407.*
Sanders et al. Comparison of cauliflower mosaic virus 35S and nopaline synthase promoters in transgenic plants. Nucleic Acids Research, 1987, vol. 15, No. 4, pp. 1543-1558.*
Kondorosi E. et al. Endoreduplication and activation of the anaphase-promoting complex during symbiotic cell development. FEBS Lett. Jun. 1, 2004;567(1):152-7. Review.*
Hill M.A. et al. Functional analysis of conserved histidines in ADP-glucose pyrophosphorylase from *Escherichia coli*. Biochem Biophys Res Commun. Mar. 17, 1998;244(2):573-7.*
Rhoads D.M. et al. Regulation of the cyanide-resistant alternative oxidase of plant mitochondria. Identification of the cysteine residue involved in alpha-keto acid stimulation and intersubunit disulfide bond formation. J Biol Chem. Nov. 13, 1998;273(46):30750-6.*
den Boer et al, Current Opinion in Biotechnology, vol. 11, pp. 138-145, 2000.

Nguyen et al, *Arabidopsis thaliana* cell cycle switch protein (At5g13840) mRNA, complete cds. EMBL BT002165 (2002).
Sasaki et al, *Oryza sativa* (japonica cultivar-group) genomic DNA, chromosome 1, PAC clone:P0698H10. EMBL AP003298 (2001).
Wing et al, *Oryza sativa* (japonica cultivar-group) chromosome 3 clone OJ1126B12, complete sequence. EMBL AC098695, 2001.
Kondorosi et al, "Endoreduplication and activation of the anaphase-promoting complex during symbiotic cell development", FEBS Lett. Jun. 1, 2004;567(1):152-7. Review.
Hill et al, Functional analysis of conserved histidines in ADP-glucose pyrophosphorylase from *Escherichia coli*. Biochem Biophys Res Commun. Mar. 17, 1998; 244(2):573-7.
Rhoads et al, Regulation of the cyanide-resistant alternative oxidase of plant mitochondria. Identification of the cysteine residue involved in alpha-keto acid stimulation and intersubunit disulfide bond formation. J. Biol Chem. Nov. 13, 1998;273(46):30750-6.
Cebolla et al, "The mitotic inhibitor ccs52 is required for endoreduplication and ploidy-dependent cell enlargement in plants", EMBO J. Aug. 16, 1999;18(16):4476-84.
Norris et al, "The intron of *Arabidopsis thaliana* polyubiquitin genes is conserved in location and is a quantitative determinant of chimeric gene expression", Plant Mol Biol. Mar. 1993;21(5):895-906.
Binet et al, "Structure and expression of sunflower ubiquitin genes", Plant Mol Biol. Sep. 1991;17(3)395-407.
Sanders et al, "Comparison of cauliflower mosaic virus 35S and nopaline synthase promoters in transgenic plants", Nucleic Acids Research, 1987, vol. 15, No. 4, pp. 1543-1558. International Search Report of PCT/IB2004/000970, mailed 1 Oct. 2004.
Cebolla et al., "The mitotic inhibitor ccs52 is required for endoreduplication and ploidy-dependent cell enlargement in plants", EMBO Journal, vol. 18, No. 16, 1999, pp. 4476-4484, XP002125116.
Nguyen et al., "Arabidopsis thaliana putative fizzy-related protein (At4g22910) mRNA, complete cds.", Database EMBL, May 7, 2002, XP002250756, Database accession No. AY099585.
Bevan et al., "*Arabidopsis thaliana* DNA chromosome 4, BAC clone F7H19 (ESSA project)", Database EMBL, Jul. 3, 1998, XP002250757, Database accession No. AL031018.
Database EMBL, Dec. 9, 2001, "*Arabidopsis thaliana* putative Srwl protein (At4g11920) mRNA, complete cds.", XP002250758, Database accession No. AY063875.
Favery et al., "The endosymbiosis-induced genes EN0D40 and CCS52a are involved in endoparasitic-nematode interactions in *Medicago truncatula*.", Molecular Plant-Microbe Interactions, vol. 15, No. 10, Oct. 2002, pp. 1008-1013, XP008020613.
Foucher et al., "Cell cycle regulation in the course of nodule organogenesis in *Medicago*.", Plant Molecular Biology, vol. 43, No. 5-6, Aug. 2000, pp. 773-786, XP002250666.
Joubes et al., "Endoreduplication in higher plants", Plant Molecular Biology, vol. 43, No. 56, Aug. 2000, pp. 735-745, XP002240147.
Li et al., "Comparison of promoters and selectable marker genes for use in Indica rice transformation", Molecular Breeding: New Strategies in Plant Improvement, vol. 3, No. 1, 1997, pp. 1-14, XP002162549.

* cited by examiner

*Primary Examiner* — Cynthia Collins

(74) *Attorney, Agent, or Firm* — Connolly Bove Lodge & Hutz LLP

(57) ABSTRACT

The present invention concerns a method for improving plant growth characteristics by increasing expression in a plant of a nucleic acid encoding a CCS52 protein and/or by increasing level and/or activity in a plant of a CCS52 protein. The invention also relates to transgenic plants having improved growth characteristics, such as increased plant size, increased organ size or increased number of organs, which plants have increased expression of a nucleic acid encoding a CCS52 protein.

27 Claims, 15 Drawing Sheets

Wild type        Transgenic: pUBI::AtCCS52A1

Wild type        Transgenic: pUBI::AtCCS52A1

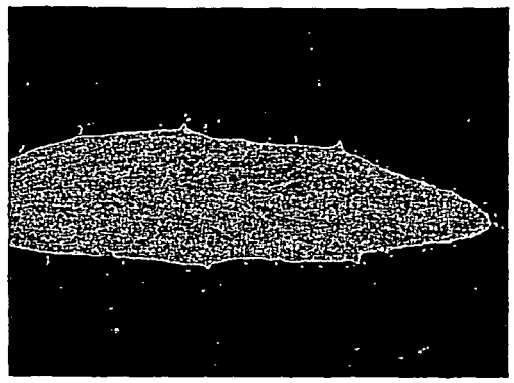
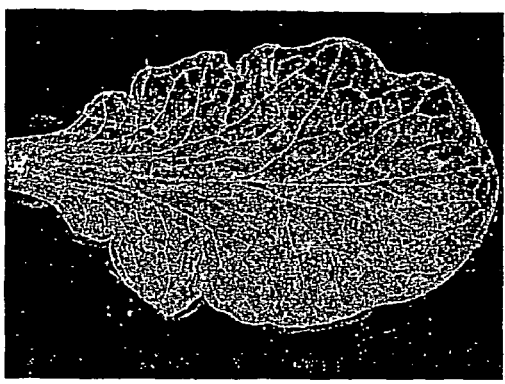
Wild type          Transgenic: pUBI::AtCCS52A1
FIGURE 5
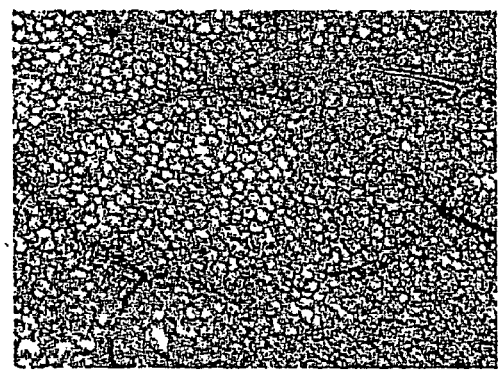
Wild type          Transgenic: pUBI::AtCCS52A1
FIGURE 6

A Wild type
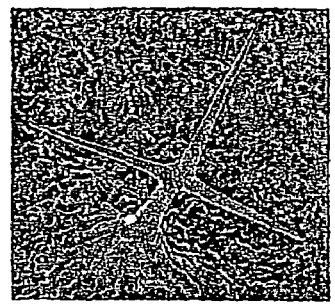
B Transgenic: pUBI::AtCCS52A1
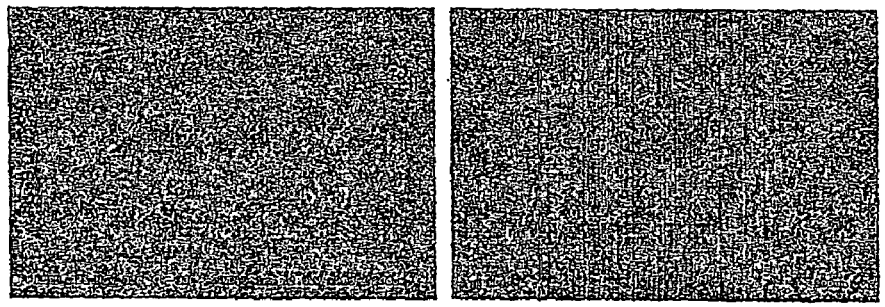
FIGURE 7
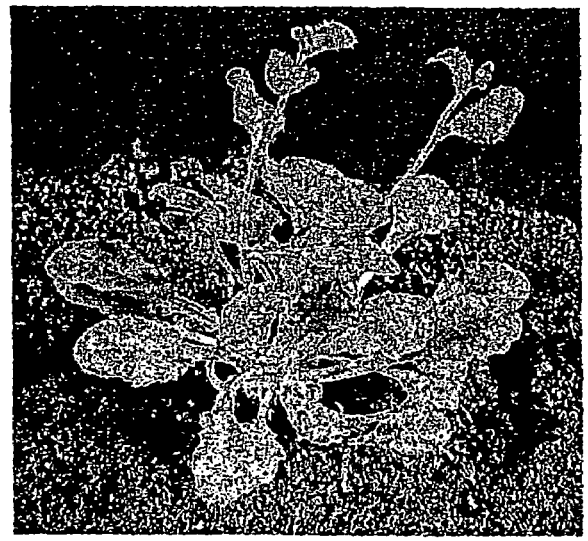
Wild type          Transgenic: p2S2::AtCCS52A1
FIGURE 8

CCS52 motifs

| Gene | C-box | Motif 1 |
|---|---|---|
| AtCCS52A1 (At4g22910) | 62 DRFIPSR 68 | 70 GSNFALFDL 78 |
| AtCCS52A2 (At4g11920) | 53 DRFIPSR 59 | 61 GSNFALFDL 69 |
| AtCCS52B (At5g13840) | 46 DRFIPCR 52 | 54 SSRLHAFDL 62 |
| Rice CCS52A (AK070642) | 52 DRFIPSR 58 | 60 GSNLALFDL 68 |
| Consensus | DRFIPXR | XSXXXXFDL |
| SEQ ID NO | SEQ ID NO 16 | SEQ ID NO 7 |

| Motif 2 | Motif 3 | Motif 4 |
|---|---|---|
| 88 EDGAGSYATLLRAAMFG 104 | 117 SSRNIFRFKTETHRSL 133 | 207 SKVTKL 211 |
| 81 EDGAGSYASLLKTALFG 97 | 111 SPSGNIFRFKTETQRSL 127 | 198 SKVTKL 202 |
| 73 EGGNEAYSRLLKSELFG 89 | 111 SPCTNMLRFKTDRSNS 129 | 203 SKVTKL 207 |
| 93 TPASSPYCALLRAALFG 109 | 137 PATGNIFRFKAEVPRNA 152 | 228 SKVTKL 232 |
| XXXXXYXXLLXXXXFG | XXXXNXXRFKX(2 or 4)RXX | SKVTKL |
| SEQ ID NO 8 | SEQ ID NO 9 | SEQ ID NO 10 |

| Motif 5 | Motif 6 |
|---|---|
| 289 DHVSKLAGHKS 300 | 329 HSTQPVLKYSEH 340 |
| 283 DHVSKLKGHKS 293 | 330 HSTQPVLRFCEH 341 |
| 288 DFVSKLVGHKS 298 | 335 HSQQPILKLTEH 346 |
| 313 DYISRLAGHKS 323 | 352 HSAHPVLKYTEH 363 |
| DXXSXLXGHKS | HSXXPXLXXXEH |
| SEQ ID NO 11 | SEQ ID NO 12 |

| Motif 7 | Motif 8 | Motif 9 |
|---|---|---|
| 371 WNTTTNTHLSSIDT 384 | 403 LYLAVSPDGQTIVT 416 | 471 EIGSSFFGRTTIR 483 |
| 364 WNTTTNTHLNCVDT 377 | 426 LYLAVSPDGQTIVT 439 | 463 EIGALSFGRTTIR 476 |
| 369 WNTTNGNQLNSIDT 382 | 431 LYLATSPDGQTIVT 444 | 469 DTGLWSLGLTQIR 481 |
| 394 WNTTTNMHLNCVDT 107 | 456 LYLAISPDGQTIVT 469 | 495 SIGATSFVRSYIR 508 |
| WNTTXXXXLXXXDT | LYLAXSPDGQTIVT | XXGXXXXXXXXIR |
| SEQ ID NO 13 | SEQ ID NO 14 | SEQ ID NO 15 |

FIGURE 13

SEQ ID NO 1: Arabidopsis thaliana CCS52A1 cDNA, At4g22910

ATGGAAGAAGAAGATCCTACAGCAAGCAATGTGATAACGAATTCGAATTCTTCATCTATGAG
AAACCTATCGCCGGCGATGAATACTCCGGTGGTTTCACTTGAGTCACGAATCAATCGATTAA
TCAATGCTAATCAATCTCAATCACCATCACCATCATCACTATCAAGGTCTATATACTCTGAT
AGATTTATCCCCAGTAGATCCGGATCCAATTTCGCTCTTTTCGATCTATCTCCTTCTCCTAG
TAAAGATGGTAAGGAAGATGGAGCTGGCTCTTACGCTACTCTGTTGCGTGCGGCGATGTTTG
GTCCTGAGACGCCGGAGAAGAGAGATATTACTGGGTTTTCTTCTTCCAGGAATATTTTAGG
TTTAAGACGGAGACTCATCGGTCTTTGAATTCGTTTTCTCCTTTTGGTGTTGATGATGATTC
TCCTGGTGTTTCTCATAGTGGTCCTGTTAAAGCTCCCAGGAAAGTGCCGCGATCGCCGTATA
AGATTCTTGATCTCGTTGACTTTAGATCTTTGGTTTCGATAATGCATGAAACAATTTGTGAT
CTTTGTGATGTTTTGGTCTCTGAGGGTCTAGAATTTGAGTCTGAGGTATTGGATGCACCGGC
CTTGCAAGATGATTTTATCTGAATCTTGTGGATTGGTCTGCACAAAATGTTCTAGCAGTGG
GACTAGGGAACTGTGTGTATTTATGGAATGCTTGTAGCAGCAAGGTTACTAAGTTATGTGAT
CTCGGAGCTGAGGATAGTGTTTGCTCAGTGGGTTGGGCGTTACGTGGAACTCATCTGGCTGT
TGGAACTAGTACCGGGAAAGTTCAGATATGGGATGCGTCACGCTGCAAGAGAACAAGAACAA
TGGAAGGTCATCGTCTAAGAGTTGGAGCCCTGGCATGGGGTTCATCGGTTCTGTCATCTGGT
AGCAGAGACAAGAGTATTCTTCAGAGAGACATAAGGTGTCAAGAAGATCATGTCAGTAAATT
GGCAGGTCATAAATCTGAGGTATGCGGACTCAAGTGGTCTTATGACAACAGAGAGCTAGCAT
CTGGTGGAAACGACAATAGGCTTTTTGTATGGAACCAACATTCAACACAACCGGTTTTGAAA
TATAGTGAACACACTGCAGCTGTTAAAGCCATTGCTTGGTCTCCTCATGTTCATGGGCTTCT
TGCTTCTGGTGGTGGTACTGCTGATAGATGCATACGTTTTTGGAATACAACCACGAATACTC
ATTTAAGTTCCATAGATACTTGCAGTCAGGTATGCAATCTAGCTTGGTCTAAGAACGTAAAC
GAGCTTGTTAGCACACACGGATACTCTCAGAACCAAATCATTGTCTGGAAATACCCAACCAT
GTCCAAAATTGCTACTCTAACCGGTCACACATACCGAGTCTTATACCTTGCGGTTTCACCCG
ATGGACAGACGATTGTAACAGGAGCAGGAGATGAAACCTTAAGGTTCTGGAATGTTTTCCCT
TCCCCAAAATCTCAGAACACGGATAGTGAAATCGGGTCGTCTTTCTTTGGTAGAACAACAAT
TCGGTGAGAAGTTACTTTCAAAACACACAGAAAAAGTCATAAATTCTTGATTTCTTCAGCAG
CAGCCAGCTTGAGTTGGTCGTCTCAACCAACTTTTTTCACACGGGAGCAGAGAGTCATTAAA
TTCTTTTACACACGGATGCAACAAGATCTAACCCTTTTGATTTAATCACGATCTTTGGGTTT
CCATCAAGATGCACAACATTTTCCCCCAAAATTTTCCAAAGTGTATATCTTTATTCAATTTT
TCTTCATATATCAAAATATAGTTTCTTTTGTATTTATTTACTTACGAACACAACATTTTATA
AAATAAGCCCATGATAATAATGCAATAATTCGTTACCATTCTCTT

SEQ ID NO 2: Arabidopsis thaliana CCS52A1 protein

MEEEDPTASNVITNSNSSSMRNLSPAMNTPVVSLESRINRLINANQSQSPSPSSLSRSIYSD
RFIPSRSGSNFALFDLSPSPSKDGKEDGAGSYATLLRAAMFGPETPEKRDITGFSSSRNIFR
FKTETHRSLNSFSPFGVDDDSPGVSHSGPVKAPRKVPRSPYKILDLVDFRSLVSIMHETICD
LCDVLVSEGLEFESEVLDAPALQDDFYLNLVDWSAQNVLAVGLGNCVYLWNACSSKVTKLCD
LGAEDSVCSVGWALRGTHLAVGTSTGKVQIWDASRCKRTRTMEGHRLRVGALAWGSSVLSSG
SRDKSILQRDIRCQEDHVSKLAGHKSEVCGLKWSYDNRELASGGNDNRLFVWNQHSTQPVLK
YSEHTAAVKAIAWSPHVHGLLASGGGTADRCIRFWNTTTNTHLSSIDTCSQVCNLAWSKNVN
ELVSTHGYSQNQIIVWKYPTMSKIATLTGHTYRVLYLAVSPDGQTIVTGAGDETLRFWNVFP
SPKSQNTDSEIGSSFFGRTTIR

FIGURE 14 −1

SEQ ID NO 3: Oryza sativa CCS52A cDNA, AK070642

ATCCCCAAATCTCTCGCCCCCACCCATGGATCACCACCACCACCACCTGCCGCCGCCGCCGC
CGCGGTCGCCGATGGAGAACTCCGCGTCCTCCAAGCCGCCCACCCCGGCGTCCACCCCGTCG
TCGCGCCTCGCCGCCGCGCCGTCCTCCCGCGTCTCCTCCGCGGCGCCGCACCCCTCCCCGTC
CTCCTCCGCGCCCACGCCGGCCTCGCGGACGGTCTACAGCGACCGCTTCATCCCCAGCCGCG
CCGGATCCAACCTCGCGCTCTTCGACCTCGCCCCGTCGCCGTCCCACCACGACGCCGCCGCC
GCCGCCGCCTCCCCCGGCGCGCCGCCCCCTCCGGATCTACCCCGGCCTCGTCGCCCTACTG
CGCGCTCCTCCGCGCCGCGCTCTTCGGCCCCACCACGCCCGACCGGGTGGCGTCGTCGGCGT
CCGCGTGCTCCTCCTCCTCCTCCGCCGGGGCGTCGCCCGTGGGCTCACCCGCCACCGGCAAC
ATATTCAGGTTCAAGGCGGAGGTGCCCCGGAATGCTAAGCGCGCCCTTTTCTCCGACGGGGA
CGACGAGGGCGTGCTCTTCCCCGGGGTGTTCACGACGAGGGGCACTGGCCCCAGGAAGATCC
CTAGGTCACCTTATAAGGTGCTGGATGCTCCGCATTGCAGGATGACTTCTACCTGAACCTT
GTGGATTGGTCTTCGCATAATATCCTTGCAGTTGGATTGGGGAATTGTGTCTACTTATGGAA
TGCATGCAGCAGCAAGGTCACCAAGCTATGTGATTTGGGGGTGGATGACAATGTCTGTTCAG
TGGGTTGGGCACAGCGTGGCACTCACCTTGCTGTAGGGACAAACCAAGGCAAAGTTCAGGTA
TGGGATGCCACTCGTTGTAAGAGAATAAGAACCATGGAAAGCCATCGGATGCGAGTAGGTGC
TCTTGCATGGAATTCATCATTGCTTTCGTCAGGCAGTCGTGACAAGAGCATCCTTCACCATG
ATATCCGTGCCCAGGATGATTATATTAGTAGACTTGCTGGGCATAAATCGGAGGTCTGTGGG
CTCAAGTGGTCTTATGATAACCGTCAGCTTGCATCTGGTGGTAATGACAACAGACTTTATGT
ATGGAATCAACACTCGGCGCACCCGGTACTGAAGTATACTGAGCATACAGCAGCTGTCAAAG
CTATTGCGTGGTCACCTCATCTTCATGGGCTGCTTGCATCTGGTGGAGGAACTGCAGATAGA
TGCATACGATTTTGGAATACCACCACGAATATGCACTTAAATTGCGTCGACACAGGCAGTCA
GGTCTGTAATCTTGTATGGTCAAAGAATGTTAATGAGCTTGTTAGCACTCATGGATATTCTC
AAAATCAGATAATTGTTTGGCGATACCCAACAATGTCAAAGCTCGCCACATTGACAGGCCAT
ACATATAGGGTATTATATTTAGCCATCTCCCCAGATGGACAGACTATAGTAACTGGCGCTGG
TGATGAAACGCTTCGGTTTTGGAACGTGTTTCCATCTCCCAAGTCCCAGAGTTCTGACAGCC
TAAGTAGCATCGGGGCCACATCATTTGTTAGGAGCTACATCCGGTGACACTGAGATGTGGTA
ATCTAATAACACTTGGCTCATAAGTCATAACACTACTGCAGCAGAGTGTTGATGATCATCAA
TATCATTCCATTTGTACCACTTGCATCACCAGTTCATGAACCATCAAACCTAGCCAAATTTT
AGAGATAGTAGGATGCAGAATGGTGAAACTGGCTCGCAGACCTCGGAGTGGCTCATTTGCTG
AATGCTGTATATATTTATTCATTGGCTTTGTAGGAGCGAAGATGGCAAACACTGACCATCCG
CAATGTACCATTGATAAGTTCACGGCCTCCTGTTTTTGTTTTTGCTGAGTCAACTTGGAGCT
GGAGCTCTTATGTATACCATGCTAGGGCTTAACAACATTGGCCAACTCATGATGCTCATTGC
ATCCAAGTTGGAATATGCTAAGGAAGCTGGAGAATTTCTGGTGC

SEQ ID NO 4: Oryza sativa CCS52A protein

MENSASSKPPTPASTPSSRLAAAPSSRVSSAAPHPSPSSSAPTPASRTVYSDRFIPSRAGSN
LALFDLAPSPSHHDAAAAASPGAPPPSGSTPASSPYCALLRAALFGPTTPDRVASSASACS
SSSSAGASPVGSPATGNIFRFKAEVPRNAKRALFSDGDDEGVLFPGVFTTRGTGPRKIPRSP
YKVLDAPALQDDFYLNLVDWSSHNILAVGLGNCVYLWNACSSKVTKLCDLGVDDNVCSVGWA
QRGTHLAVGTNQGKVQVWDATRCKRIRTMESHRMRVGALAWNSSLLSSGSRDKSILHHDIRA
QDDYISRLAGHKSEVCGLKWSYDNRQLASGGNDNRLYVWNQHSAHPVLKYTEHTAAVKAIAW
SPHLHGLLASGGGTADRCIRFWNTTTNMHLNCVDTGSQVCNLVWSKNVNELVSTHGYSQNQI
IVWRYPTMSKLATLTGHTYRVLYLAISPDGQTIVTGAGDETLRFWNVFPSPKSQSSDSLSSI
GATSFVRSYIR

FIGURE 14 – 2

SEQ ID NO 5: Oryza sativa genomic DNA encoding CCS52B protein, AP003298

ATGCTAATGGGCCGGCCCGCATGGCAGAGAGAGTACAACGGCTACTCGGGTGGGGGGCCCAC
AGTCAGAGGGAGACAGCTCGTGCTAGAAAAAGTAGGCGACTTGCCCACTCCAACCAAAGTGA
CCGTTGCAACCTCATCTCCGCTCCTCTTCCTCCTCCTCGTCGTCGTTGTCGTCGTCGGCGGC
GCATCCAGCCTCGACGTGCCGGCGGCGCCGGCGCCGCCGCGCCTCAACGTGCCGCCGGCGAT
GGCGGGGGGGCTCCGCCTCGATCCCGCCGTCGCCTCCCCGGCCCGCCTCCTCCTCGACGTCC
CCAAGACGCCATCCCCTTCCAAGACCACGTACAGCGACCGCTTCATCCCCTGCCGCTCCTCC
TCCCGCCTCCACAACTTCGCCCTCCTCGACCGCGACCGCGCCTCCCCCTCCTCCACCACCGA
CGACGCCCCCTACTCCCGCCTCCTCCGCGCCGAGATCTTCGGCCCGGACTCCCCCTCCCCGG
CTCCCTCCTCCCCAACACCAACCTCTTCCGCTTCAAGACCGACCACCCCTCGCCCAAATCG
CCCTTCGCCGCCTCCGCCGCCGCCACCGCCGGCCACTACGACTGCACCGCCGGCTCCGCTGA
ATCCTCCACGCCGCGCAAGCCGCCCAGGAAGGTCCCCAAGACCCCGCACAAGGTCCTGGACG
CGCCGTCGCTGCAGGACGACTTCTACCTCAATCTTGTCGACTGGTCGTCGCAGAACACGCTC
GCCGTCGGCCTCGGGAATTGCGTCTACCTCTGGTCGGCTTCCAATTGCAAGGTCACCAAGCT
CTGCGATTTGGGGCCCAGGGACAGCGTCTGCGCTGTGCACTGGACCCGAGAAGGCTCCTATC
TTGCCATCGGCACCAGCCTTGGCGATGTCCAGATTTGGGATAGCTCTCGCTGTAAACGGATT
AGGAACATGGGAGGACACCAAACACGGACTGGTGTATTAGCATGGAGCTCCCGAATCTTGTC
CTCCGGTAGCAGGGACAAGAACATATTGCAGCATGACATCCGTGTCCCAAGTGACTATATCA
GCAAGTTCTCAGGGCACAGATCAGAGAACCATGTATGTGCATCAAGTGACAGTTTTTTTGGT
CAGGTCTGTGGACTGAAATGGTCGCACGACGACCGTGAGCTTGCATCCGGTGGAAATGATAA
TCAGCTGCTAGTATGGAACCAACGTTCGCAGCAGCCGATATTGAGGCTGACAGAACACACAG
CTGCAGTTAAAGCAATAGCATGGTCACCACATCAGCAAGGCCTCCTGGCATCAGGTGGTGGA
ACCGCTGATAGGTGTATCAGGTTCTGGAACACGGTTAATGGAAACATGCTGAATTCAGTGGA
CACAGGCAGCCAGGCGACTTGTGAGCACTCATGGGTATTCCCAAAACCAAATCATGGTGTGG
AAGTACCCATCTATGTCAAAGGTTGCTACTCTAACTGGACACACGCTGCGAGTGCTTTACCT
TGCAATGTCACCACAATAGTAACAGGAGCCGGGGATGAAACCCTCAGATTTTGGAATATTTT
TCCTTCAATGAAGACACAGGTAGGCATCTATTGTTGA

SEQ ID NO 6: Oryza sativa CCS52B protein, BAB98864

MLMGRPAWQREYNGYSGGGPTVRGRQLVLEKVGDLPTPTKVTVATSSPLLFLLLVVVVVVGG
ASSLDVPAAPAPPRLNVPPAMAGGLRLDPAVASPARLLLDVPKTPSPSKTTYSDRFIPCRSS
SRLHNFALLDRDRASPSSTTDDAPYSRLLRAEIFGPDSPSPAPSSPNTNLFRFKTDHPSPKS
PFAASAAATAGHYDCTAGSAESSTPRKPPRKVPKTPHKVLDAPSLQDDFYLNLVDWSSQNTL
AVGLGNCVYLWSASNCKVTKLCDLGPRDSVCAVHWTREGSYLAIGTSLGDVQIWDSSRCKRI
RNMGGHQTRTGVLAWSSRILSSGSRDKNILQHDIRVPSDYISKFSGHRSENHVCASSDSFFG
QVCGLKWSHDDRELASGGNDNQLLVWNQRSQQPILRLTEHTAAVKAIAWSPHQQGLLASGGG
TADRCIRFWNTVNGNMLNSVDTGSQATCEHSWVFPKPNHGVEVPIYVKGCYSNWTHAASALP
CNVTTIVTGAGDETLRFWNIFPSMKTQVGIYC

SEQ ID NO 7: consensus motif 1 of CCS52 protein

XSXXXXFDL

FIGURE 14 – 3

SEQ ID NO 8: consensus motif 2 of CCS52 protein

XXXXXXYXXLLXXXXFG

SEQ ID NO 9: consensus motif 3 of CCS52 protein

XXXXNXXRFKX(2 or 4)RXX

SEQ ID NO 10: consensus motif 4 of CCS52 protein

SKVTKL

SEQ ID NO 11: consensus motif 5 of CCS52 protein

DXXSXLXGHKS

SEQ ID NO 12: consensus motif 6 of CCS52 protein

HSXXPXLXXXEH

SEQ ID NO 13: consensus motif 7 of CCS52 protein

WNTTXXXXLXXXDT

SEQ ID NO 14: consensus motif 8 of CCS52 protein

LYLAXSPDGQTIVT

SEQ ID NO 15: consensus motif 9 of CCS52 protein

XXGXXXXXXXXIR

SEQ ID NO 16: consensus C box

DRFIPXR

SEQ ID NO 17: consensus motif 1 of CCS52A proteins

GSN(F/L)ALFD(L/I)

SEQ ID NO 18: prm03191

GGGGACAAGTTTGTACAAAAAAGCAGGCTTCACAATGGAAGAAGAAGATCCTACAGC

SEQ ID NO 19: prm01392

GGGGACCACTTTGTACAAGAAAGCTGGGTTTCTCACCGAATTGTTGTTCTAC

FIGURE 14 –4

PLANTS HAVING IMPROVED GROWTH CHARACTERISTICS AND A METHOD FOR MAKING THE SAME

The present application is a continuation of application Ser. No. 10/551,696 (published as US 2007-0067875 A1 on Mar. 22, 2007), filed Aug. 8, 2006 (pending), now abandoned which is a U.S. national phase of international application PCT/IB2004/000970, filed 31 Mar. 2004, which designated the U.S. and claims priority of EP 03290812.1, filed 31 Mar. 2003, the entire contents of each of which is hereby incorporated by reference.

The present invention concerns a method for improving plant growth characteristics. More specifically, the present invention concerns a method for improving plant growth characteristics by increasing, in a plant, expression of a cell cycle switch gene encoding a 52 kDa protein (CCS52 protein) and/or by increasing activity of the CCS52 protein itself. The present invention also concerns plants having increased expression of a nucleic acid encoding a CCS52 protein and/or increased activity of a CCS52 protein, which plants have improved growth characteristics relative to corresponding wild-type plants.

Given the ever-increasing world population, it remains a major goal of agricultural research to improve the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogenous genetic complements that may not always result in the desirable trait being passed on from parent plants. In contrast, advances in molecular biology have allowed mankind to more precisely manipulate the germplasm of plants. Genetic engineering of plants entails the isolation and manipulation of genetic material (typically in the form of DNA or RNA) and the subsequent introduction of that genetic material into a plant. Such technology has led to the development of plants having various improved economic, agronomic or horticultural traits. A trait of particular economic interest is high yield.

The ability to improve one or more plant growth characteristics, would have many applications in areas such as crop enhancement, plant breeding, production of ornamental plants, arboriculture, horticulture, forestry, production of algae or plants (for use as bioreactors for example, for the production of pharmaceuticals, such as antibodies or vaccines, or for the bioconversion of organic waste, or for use as fuel, in the case of high-yielding algae and plants).

CCS52 belongs to a small group of proteins containing several WD repeat motifs and is the plant homologue of animal APC activators involved in mitotic cyclin degradation (WO99/64451). In Cebolla et al. (EMBO J., 1999, 18: 4476-84), the isolation of CCS52 clones from *Medicago sativa* root nodules was reported and CCS52 was described to be part of a small gene family that appears to be conserved in plants. Furthermore, the functional domains and regulation mechanisms of CCS52 proteins have been described in detail by Tarayre et al. (The plant Cell, 2004, vol 16, 422-434).

In document WO99/64451 K was suggested that down-regulation of CCS52 expression pushes the cells towards proliferation and that overproduction of CCS52 pushes the cells towards differentiation. Also, in the document in the name of Kondorosi et al. (1999, The EMBO J. 18 (16), p. 4476-4484), it is stated that expression of CCS52 may switch proliferating cells to differentiation programs. For some cells differentiation means endoreduplication. This switch to differentiation (or endoreduplication) clearly involves an arrest in proliferation, thus an arrest in cell division. These data were in line with earlier findings in yeast that teach when CCS52 is used to increase differentiation (or endoreduplication), a cell cycle arrest is inevitably triggered. Therefore, the effect on endoreduplication on the one hand, namely the increased cell size, is inherently linked to a reduction of cell number due to cell division arrest. The results obtained in *Medicago* and *Arabidopsis*, for CCS52 overexpression driven by the CaMV35S promoter corroborated this view.

The examples in document WO99/64451 show that *Medicago* plants expressing an anti-sense version of a *Medicago* CCS52 gene form fewer seeds and fewer lateral branches. Furthermore, constructs for overexpression of a *Medicago* CCS52 gene, under control of a strong constitutive promoter (CaMV35S), have been disclosed and were used to transform *Medicago* plants. Although it was indicated that overexpression of a CCS52 gene under the control of a CaMV35S promoter resulted in a positive effect on somatic embryogenesis, no plants were regenerated and no further positive effects were observed. To the contrary, evidence has been presented that overexpression of CCS52 under the control of a CaMV35S promoter is detrimental. This detrimental effect was first observed in *Medicago* transgenic plants. Later, this detrimental effect was also observed in *Arabidopsis thaliana* transformed with the *Arabidopsis* CCS52 gene under control of a CaMV35S promoter.

Therefore, the prior art does not teach how the CCS52 gene can be used to improve plant growth characteristics, and so far only negative results with respect to the use of CCS52 for growth improvement have been obtained.

Unexpectedly, it has now been found that, in contrast to earlier observations, overexpression of a CCS52 gene does not cause a detrimental effect. Moreover, it has now been found that plant growth characteristics may even be improved by the methods of the present invention. These improved growth characteristics are obtained when overexpression of a CCS52 gene in a plant is controlled by an medium-strength promoter.

Further surprisingly, it has also been found that plants made by the methods of the present invention have specific characteristics such as increased plant size, increased organ size and/or increased number of organs, compared to corresponding wild-type plants.

Therefore, the present invention teaches how to improve plant growth characteristics, such as plant size, organ size and/or organ number by increased expression in a plant of a nucleic acid encoding a CCS52 protein.

According to a first embodiment of the present invention, there is provided a method to improve plant growth characteristics relative to corresponding wild-type plants, comprising the introduction into a plant of a nucleic acid encoding a CCS52 protein, under control of a medium-strength promoter.

The introduction into a plant of a nucleic acid encoding a CCS52 protein under control of a medium-strength promoter, may result in an increased expression of the nucleic acid encoding a CCS52 protein. Additionally, this introduction may result in an increased level and/or activity of the CCS52 protein.

Advantageously, and according to a preferred embodiment of the present invention, increased expression of a nucleic acid encoding a CCS52 protein and/or increased level and/or activity of the CCS52 protein itself may be effected by a direct recombinant approach, for example, by transforming the plant with a nucleic acid encoding a CCS52 protein or a variant thereof.

Alternatively, increased expression of a nucleic acid encoding a CCS52 protein and/or increased level and/or activity of the CCS52 protein itself may be effected by an indirect recombinant approach, for example, by transforming a plant to modify the expression of a CCS52 gene already in that plant, which CCS52 gene may be endogenous or a transgene (previously) introduced into the plant. This may be effected by the inhibition or stimulation of regulatory sequences that drive expression of the endogenous gene or transgene. Such regulatory sequences may be introduced into a plant. For example, a medium-strength promoter may be introduced into a plant to drive the endogenous CCS52 gene, which medium-strength promoter may be heterologous to the endogenous CCS52 gene; Heterologous being not naturally occurring in the nucleic acid sequences flanking the CCS52 coding region when it is in its biological genomic environment.

The term "CCS52 protein" as used herein encompasses a cell cycle switch gene encoding a 52 kDa protein and this term also encompasses variants thereof. Examples of CCS52 proteins are herein represented by SEQ ID NO 2, 4 or 6. Other examples of CCS52 proteins are described in Cebolla et al. (EMBO 1999, vol. 18(16) 4476-4484) and in Tarayre et al. (The plant cell, 2004, vol. 16: 422-434). The terms "CCS52 nucleic acid" or "CCS52 gene" or "nucleic acid encoding a CCS52 protein" are used interchangeably herein and encompass, for example, nucleic acids as represented by SEQ ID NO 1, 3 or 5, or variants thereof. A variant CCS52 protein or a variant nucleic acid encoding a CCS52 protein include:

(i) Functional portions of a CCS52 nucleic acid, for example of SEQ ID NO 1, 3 or 5;
(ii) Nucleic acids capable of hybridising with a CCS52 nucleic acid, for example with SEQ ID NO 1, 3 or 5;
(iii) Alternative splice variants of a CCS52 nucleic acid, for example of SEQ ID NO 1, 3 or 5;
(iv) Allelic variants of a CCS52 nucleic acid, for example of SEQ ID NO 1, 3 or 5;
(v) Homologues of a CCS52 protein, for example of SEQ ID NO 2, 4 or 6;
(vi) Derivatives of a CCS52 protein, for example of SEQ ID NO 2, 4 or 6; and
(vii) Active fragments of a CCS52 protein, for example of SEQ ID NO 2, 4 or 6.

According to a preferred embodiment, such variants are (or encode) proteins having at least one of the conserved CCS52 motifs as described hereinafter.

According to a preferred embodiment, such variants are (or encode) proteins having CCS52 activity, or are (or encode) proteins that retain similar biological activity or at least part of the biological activity of a CCS52 protein. The biological activity of a CCS52 protein may be tested as described in Cebolla et al., 1999. This test involves overexpressing the CCS52 or variant in *Saccharomyces pombe*. The phenotypes of the transformed yeast cells are compared with the phenotypes of yeast cells transformed with the empty vector pREP1 as negative control, and with the phenotypes of the yeast cells transformed with the pREP1-srw1$^+$ as positive control. Expression of either srw1$^+$ or CCS52 should result in growth arrest of the cells.

Advantageously, the methods according to the invention may be practised using variant CCS52 proteins and variant CCS52 nucleic acids. Suitable variants include variants of SEQ ID NO 2, 4 or 6 and/or variants of SEQ ID NO 1, 3 or 5.

The term "variant" includes variants in the form of a complement, DNA, RNA, cDNA or genomic DNA. The variant nucleic acid may be synthesized in whole or in part, it may be a double-stranded nucleic acid or a single-stranded nucleic acid. Also, the term "variant" encompasses a variant due to the degeneracy of the genetic code, a family member of the gene or protein and variants that are interrupted by one or more intervening sequences, such as introns, spacer sequences or transposons.

One variant nucleic acid encoding a CCS52 protein is a functional portion of a nucleic acid encoding a CCS52 protein. Advantageously, the method of the present invention may also be practised using a portion of a nucleic acid encoding a CCS52 protein. A functional portion refers to a piece of DNA derived from an original (larger) DNA molecule, which portion, retains at least part of the functionality of the original DNA, which functional portion, when expressed in a plant, gives plants having improved growth characteristics. The portion may be made by one or more deletions and/or truncations of the nucleic acid. Techniques for making such deletions and/or truncations are well known in the art. Portions suitable for use in the methods according to the invention may readily be determined by following the methods described in the Examples section by simply substituting the sequence used in the actual Example with the portion.

Another variant of a nucleic acid encoding a CCS52 protein is a nucleic acid capable of hybridising with a nucleic acid encoding a CCS52 protein, for example with any of the nucleic acids as represented by SEQ ID NO 1, 3 or 5. Hybridising sequences suitable for use in the methods according to the invention may readily be determined, for example by following the methods described in the Examples section by simply substituting the sequence used in the actual Example with the hybridising sequence.

The term "hybridising" as used herein means annealing to a substantially homologous complementary nucleotide sequences in a hybridization process. The hybridisation process may occur entirely in solution, i.e. both complementary nucleic acids are in solution. Tools in molecular biology relying on such a process include the polymerase chain reaction (PCR; and all methods based thereon), subtractive hybridisation, random primer extension, nuclease S1 mapping, primer extension, reverse transcription, cDNA synthesis, differential display of RNAs, and DNA sequence determination. The hybridisation process may also occur with one of the complementary nucleic acids immobilised to a matrix such as magnetic beads, Sepharose beads or any other resin. Tools in molecular biology relying on such a process include the isolation of poly (A+) mRNA. The hybridisation process may furthermore occur with one of the complementary nucleic acids immobilised to a solid support such as a nitrocellulose or nylon membrane or immobilised by e.g. photolithography to e.g. a siliceous glass support (the latter known as nucleic acid arrays or microarrays or as nucleic acid chips). Tools in molecular biology relying on such a process include RNA and DNA gel blot analysis, colony hybridisation, plaque hybridisation, in situ hybridisation and microarray hybridisation. In order to allow hybridisation to occur, the nucleic acid molecules are generally thermally or chemically denatured to melt a double strand into two single strands and/or to remove hairpins or other secondary structures from single stranded nucleic acids. The stringency of hybridisation is influenced by conditions such as temperature, sodium/salt concentration and hybridisation buffer composition. High stringency conditions for hybridisation include high temperature and/or low salt concentration (salts include NaCl and Na$_3$-citrate) and/or the inclusion of formamide in the hybridisation buffer and/or lowering the concentration of compounds such as SDS (sodium dodecyl sulphate detergent) in the hybridisation buffer and/or exclusion of compounds, such as dextran sulphate or polyethylene glycol (promoting molecular crowding) from the hybridisation buffer. Conventional hybridisation conditions are described in, for example, Sambrook (2001) Molecular Cloning: a laboratory manual, 3rd Edition Cold Spring Harbor Laboratory Press, CSH, New York, but the skilled craftsman will appreciate that numerous different hybridisation conditions may be designed in function of the known or the expected sequence identity and/or length of the nucleic acids. Sufficiently low stringency hybridisation conditions are particularly preferred (at least in the first instance) to isolate nucleic acids heterologous to the DNA sequences of the invention defined supra. An example of low stringency conditions is 4-6×SSC/0.1-0.5% w/v SDS at 37-45° C. for 2-3 hours. Depending on the source and concentration of the nucleic acid involved in the hybridisation, alternative conditions of stringency may be employed, such as medium stringency conditions. Examples of medium stringency conditions include 14×SSC/0.25% w/v SDS at $\geq$45° C. for 2-3 hours. Preferably, the variants capable of hybridizing with a CCS52 gene are capable of specifically hybridizing. With "specifically hybridizing" is meant hybridising under stringent conditions. An example of high stringency conditions includes 0.1-2×SSC, 0.1×SDS, and 1×SSC, 0.1×SDS at 60° C. for 2-3 hours.

The methods according to the present invention may also be practised using an alternative splice variant of a nucleic acid encoding a CCS52 protein, for example, an alternative splice variant of SEQ ID NO 1, 3 or 5. The term "alternative splice variant" as used herein encompasses variants of a nucleic acid in which selected introns and/or exons have been excised, replaced or added. Such splice variants may be found in nature or may be manmade. Methods for making such splice variants are well known in the art. Splice variants suitable for use in the methods according to the invention may readily be determined, for example, by following the methods described in the Examples section by simply substituting the sequence used in the actual Example with the splice variant.

Another variant CCS52 nucleic acid useful in practising the method for improving plant growth characteristics, is an allelic variant of a CCS52 gene, for example, an allelic variant of SEQ ID NO 1, 3 or 5. Allelic variants exist in nature and encompassed within the methods of the present invention is the use of these natural alleles. Allelic variants also encompass Single Nucleotide Polymorphisms (SNPs) as well as Small Insertion/Deletion Polymorphisms (INDELs). The size of INDELs is usually less than 100 bp. SNPs and INDELs form the largest set of sequence variants in naturally occurring polymorphic strains of most organisms. Allelic variants suitable for use in the methods according to the invention may readily be determined, for example, by following the methods described in the Examples section by simply substituting the sequence used in the actual Example with the allelic variant.

The present invention provides a method for improving plant growth characteristics, comprising increasing expression in a plant of an alternative splice variant or of an allelic variant of a nucleic acid encoding a CCS52 protein and/or by increasing the level and/or activity in a plant of a CCS52 protein encoded by an alternative splice variant or allelic variant.

One example of a variant CCS52 protein useful in practising the methods of the present invention is a homologue of a CCS52 protein. "Homologues" of a CCS52 protein encompass peptides, oligopeptides, polypeptides, proteins and enzymes having an amino acid substitution, deletion and/or insertion relative to the CCS52 protein in question and having similar biological and functional activity as the CCS52.

Homologues of a CCS52 protein may be manmade via the techniques of genetic engineering and/or protein engineering. To produce such homologues, amino acids of the protein may be replaced by other amino acids having similar properties (such as similar hydrophobicity, hydrophilicity, antigenicity, propensity to form or break $\alpha$-helical structures or $\beta$-sheet structures). Conservative substitution tables are well known in the art (see for example Creighton (1984) Proteins. W.H. Freeman and Company).

Homologues of a particular CCS52 protein may exist in nature and may be found in the same or different species or organism from which the particular CCS52 protein is derived. Two special forms of homologues, orthologues and paralogues, are evolutionary concepts used to describe ancestral relationships of genes. The term "orthologues" relates to genes in different organisms that are homologous due to ancestral relationship. The term "paralogues" relates to gene-duplications within the genome of a species leading to paralogous genes. The term "homologues" as used herein also encompasses paralogues and orthologues of a CCS52 protein, which are also useful in practising the methods of the present invention.

Another special form of a CCS52 homologue is a member of the same gene family of CCS52 proteins. It is known that AtCCS52A1 belongs to a multigene family, and therefore a person skilled in the art will recognize that the methods according to the present invention may also be practised using the encoding sequence of a family member of a CCS52 protein, such as a family member of SEQ ID NO 2, 4 or 6.

The homologues useful in the method according to the invention have in increasing order of preference, at least 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to a CCS52 protein, for example, to any one of SEQ ID NO 2, 4 or 6. Alternatively, the nucleic acid sequence encoding any one of the above-mentioned homologue may have at least 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to a CCS52 nucleic acid, for example, to any one of SEQ ID NO 1, 3 or 5.

The percentage of sequence identity as mentioned above, between proteins or nucleic acids, may be calculated using a pairwise global alignment program implementing the algorithm of Needleman-Wunsch (J. Mol. Biol. 48: 443-453, 1970), which maximizes the number of matches and keeps the number of gaps to a minimum. For calculation of the above-mentioned percentages, the program needle (EMBOSS package) may be used with a gap opening penalty of 10 and gap extension penalty of 0.1. For proteins, the blosum62 matrix with a word length of 3 is preferably used. For nucleic acids, the program needle uses the matrix "DNA-full", with a word-length of 11, as provided by the EMBOSS package. The Needleman-Wunsch algorithm is best suited for analysing related protein sequences over their full length.

The homologues useful in the methods according to the invention (the proteins or their encoding nucleic acid sequences) may be derived (either directly or indirectly (if subsequently modified) from any source as described hereinafter, provided that the sequence, when expressed in a plant, leads to improved plant growth characteristics. The nucleic acid (or protein) may be isolated from yeast, fungi, plants, algae, insects or animals (including humans). This nucleic acid may be substantially modified from its native form in composition and/or genomic environment through deliberate human manipulation.

The nucleic acid encoding a CCS52 homologue is preferably isolated from a plant. Examples of CCS52 proteins are *Arabidopsis thaliana* CCS52A1 (SEQ ID NO 2 and corresponding encoding sequence SEQ ID NO 1), *Oryza sativa* CCS52A (SEQ ID NO 4 and corresponding encoding sequence SEQ ID NO 3), and *Oryza sativa* CCS52B (SEQ ID NO 6 and corresponding genomic sequence SEQ ID NO 5).

CCS52 proteins of *Arabidopsis thaliana* and *Medicago sativa* have been subdivided into different classes (Cebolla et al., 1999, EMBO J. 18: p 4476-4484). Class CCS52A (with A1 and A2 isoforms) and class CCS52B (with the B1 isoform). These classes and isoforms are also encompassed by the term "homologue" as used herein. Advantageously, these different classes and isoforms of CCS52 proteins, or their encoding nucleic acids, may be used in the methods of the present invention. Accordingly, the present invention provides a method as described hereinabove, wherein the CCS52 nucleic acid or CCS52 protein is obtained from a plant, preferably from a dicotyledoneous plant, further preferably from the family Brassicaceae, more preferably from *Arabidopsis thaliana*. According to a further embodiment, CCS52 is CCS52A or CCS52B. According to a further embodiment of the invention, CCS52 is a CCS52A1 protein. A person skilled in the art will recognize that a "CCS52A1" is a protein being closer related to AtCCS52A1, than to AtCCS52A2 or AtCCS52B. This closer relationship may be determined by calculating percentage of sequence identity, or by comparing the presence of conserved motifs as described hereinafter.

Still other suitable CCS52 homologues and their encoding sequences may be found in (public) sequence databases. Methods for the search and identification of CCS52 protein homologues in sequence databases would be well within the realm of a person skilled in the art. Such methods, involve screening sequence databases with the sequences provided by the present invention, for example, SEQ ID NO 2, 4 or 6 (or SEQ ID NO 1, 3 or 5), preferably in a computer readable form. Useful sequence databases include, but are not limited, to Genbank (ncbi.nlm.nih gov/web/Genbank website), the European Molecular Biology Laboratory Nucleic acid Database (EMBL) (ebi.ac.uk/ebi-docs/embl-db.html webpage) or versions thereof or the MIPS database (mips.gsf.de/website). Different search algorithms and software for the alignment and comparison of sequences are well known in the art. Such software includes for example, GAP, BESTFIT, BLAST, FASTA and TFASTA. Preferably the BLAST software is used, which calculates percent sequence identity and performs a statistical analysis of the similarity between the sequences. The suite of programs referred to as BLAST programs has 5 different implementations: three designed for nucleotide sequence queries (BLASTN, BLASTX, and TBLASTX) and two designed for protein sequence queries (BLASTP and TBLASTN) (Coulson, Trends in Biotechnology: 76-80, 1994; Birren et al., GenomeAnalysis, 1: 543, 1997). The software for performing BLAST analysis is publicly available through the National Centre for Biotechnology Information.

Orthologues of a CCS52 protein in other plant species may easily be found by performing a reciprocal Blast search. This method comprises searching one or more sequence databases with a query gene or protein (for example, any one of SEQ ID NO 1 to 6), using for example, the BLAST program. The highest-ranking subject genes that result from this search are then used as a query sequence in a similar BLAST search. Only those genes that have as a highest match again the original query sequence are considered to be orthologous genes. For example, to find a rice orthologue of an *Arabidopsis thaliana* gene, one may perform a BLASTN or TBLASTX analysis on a rice database such as the Oryza sativa Nipponbare database available at the NCBI website (ncbi.nim.nih. gov). In a next step, the highest ranking rice sequences are used in a reverse BLAST search on an *Arabidopsis thaliana* sequence database. The method may be used to identify orthologues from many different species, for example, from corn.

Paralogues of a CCS52 protein in the same species may easily be found by performing a Blast search on sequences of the same species from which the CCS52 protein is derived. From the sequences that are selected by the Blast search, the true paralogues may be identified by looking for the highest sequence identity or for the highest conservation of typical CCS52 motifs as described hereinafter.

Homologues of a AtCCS52A1 protein, as represented by SEQ ID NO 2, and their encoding sequences, may be found in many different species. Examples of such homologues are presented in the phylogenetic tree in FIG. 12. The homologues are presented by their Genbank accession number. Preferred homologues to be used in the present invention are the homologues that group close to AtCCS52A1_At4g22910, for example, those homologues that group between OsAP003298.3 and Hs19_NP_057347.1. These homologues include but are not limited to Hs19_NP_057347.1, Mm_NP_062731, XL-CAA74576.1, Ggcdh1c_AAL31949, Ggcdh1b_AAL31948.1, Ggcdh1d_AAL31950, Ggcdh1a_AAL31947, Dm_NP_726941, Ag_agCP12792, Ce_NP_496075.1, Dm_NP_611B54, and the homologues grouping closest to AtCCS52A1_At4g22910, including Le_AW0030735, AtCCS52A2_At4g11920, MtCCS52A_AF134835, Gm_BG044933, Os_AK070642, Zm_AY112458, AtCCS52B_At5g13840, MsCCSB, Gm_AI736659 and Zm_AI861254. The genome sequences of *Arabidopsis thaliana* and *Oryza sativa* are now available in public databases such as Genbank and other genomes are currently being sequenced. Therefore, it is expected that further homologues will readily be identifiable by sequence alignment with any one of SEQ ID NO 1 to 6 using the programs BLASTX or BLASTP or other programs.

The above-mentioned software analyses for comparing sequences, for the calculation of sequence identity, for the search of homologues, orthologues or paralogues or for the making of a phylogenetic tree, is preferentially done with full-length sequences. Alternatively, these software analyses may be carried out with a conserved region of the CCS52 protein or nucleic acid sequence, as described hereinafter. Accordingly, these analyses may be based on the comparison and calculation of sequence identity between conserved regions, functional domains, motifs or boxes.

The identification of protein domains, motifs and boxes, would also be well within the realm of a person skilled in the art by using protein domain information as available in the PRODOM (biochem.ucl.ac.uk/bsm/dbbrowser/jj/prodom-srchjj.html webpage), PIR (pir.georgetown.edu/ website), PROSITE (au.expasy.org/PROSITE/ website) or pFAM (pFAM.wustl.edu/ website) databases. Software programs designed for such domain searching include, but are not limited to, MotifScan, MEME, SIGNALSCAN, and GENESCAN. MotifScan is a preferred software program and is available at (hits.isb-sib.ch/cai-bin/PFSCAN website, which program uses the protein domain information of PROSITE and pFAM. A MEME algorithm (Version 3.0) may be found in the GCG package; or at the sdsc.edu/MEME/meme website. SIGNALSCAN version 4.0 information is available at the biosci.cbs.umn.edulsoftware/sigscan.html webpage. GENESCAN may be found at the gnomic.stanford.edu/GENESCANW.html webpage.

Ten conserved motifs have been identified in CCS52 proteins and the consensus sequences for these motifs are represented herein by SEQ ID NO 7 to 16 (see FIG. 13). Preferably, these motifs are used to search databases and to identify homologous CCS52 sequences. The presence of these motifs (for example, as represented by SEQ ID NO 7 to 16), may be determined by screening proteins sequences for sequence identity with these consensus motifs. Another aspect of the present invention is the use of conserved CCS52 motifs as represented by ant one of SEQ ID NO 7 to 15, to identify, or to manufacture (via protein engineering or grafting of such motifs into a target protein), homologues of a CCS52 gene or protein which are capable of improving plant growth characteristics. The N-terminal conserved motif, the C-box (SEQ ID NO 16) is further described in Tarayre et al. 2004.

Preferred CCS52 homologues useful in the methods of the present invention are plant CCS52 proteins that comprise at least 4 of the aforementioned consensus motifs. Motif number 2, as represented by SEQ ID NO 8 has also been described as a N-terminal "CSM" motif in Tarayre et al., 2004. Motif number 9, as represented by SEQ ID NO 15, is presumably involved in the interaction with other proteins; it is a C-terminal IR motif, which has been described as necessary for the functionality of CCS52 in the APC complex. Furthermore, the presence of multiple conserved motifs (SEQ ID NO 7 to 16) strongly suggests that CCS52 proteins are involved in multiple interactions and that several CCS52 target genes/proteins exist. Further details on the relationship between the IR motif and the CCS52 functionality are described in Tarayre et al. (2004, Plant Cell., 16(2): 422-34), which document is herein incorporated by reference as if fully set forth.

FIG. 13 shows the individual conserved motifs of different CCS52 proteins as well as the consensus sequences thereof, which are herein represented by SEQ ID NO 7 to 16. A person skilled in the art will recognize that a CCS52 motif may deviate, by for example 1 or 2 mismatches, from the above-mentioned consensus CCS52 motifs, without losing its functionality. One example of such a deviation is number of "X" amino acids in motif 3.

As may be deducted from FIG. 13, the consensus sequences may be more defined when only taking CCS52A proteins into account. For example, for CCS52A proteins, Motif number 1 has G on position 1, N at position 3, F or L at position 4, A at position 5, L at position 6 and L or I at position 9. This consensus Motif 1 for CCS52A proteins is represented herein by SEQ ID NO 17. For CCS52A proteins, Motif number 7 has T at position 5 and H at position 8. Also, for CCS52A proteins, Motif number 9 has "I" at position 2 and "R" at position 9.

Some of the variants as mentioned hereinabove may occur in nature and may be isolated from nature. Once the sequence of a variant is known, and its corresponding encoding sequence, the person skilled in the art will be able to isolate the corresponding CCS52 gene or variant from biological material such as genomic libraries, for example, by the technique of PCR. One example of such an experiment is outlined in Example 1. Alternatively, when the exact sequence is not known, new CCS52 proteins may be isolated from biological material via hybridization techniques based on probes from known CCS52 proteins.

Alternatively and/or additionally, some variants as mentioned above may be manmade via techniques involving, for example, mutation (substitution, insertion or deletion) or derivation. These variants are herein referred to as "derivatives", which derivatives are also useful in the methods of the present invention. Derivatives of a protein may readily be made using peptide synthesis techniques well known in the art, such as solid phase peptide synthesis and the like, or by protein engineering via recombinant DNA manipulations. The manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

One example of a derivative is a substitutional variant. The term "substitutional variants" of a CCS52 protein refers to those variants in which at least one residue in an amino acid sequence has been removed and a different amino acid inserted in its place. Amino acid substitutions are typically of single residues, but may be clustered depending upon functional constraints placed upon the polypeptide; insertions usually are of the order of about 1-10 amino acids, and deletions can range from about 1-20 amino acids. Preferably, amino acid substitutions comprise conservative amino acid substitutions.

Other derivatives are "insertional variants" in which one or more amino acids are introduced into a predetermined site in the CCS52 protein. Insertions may comprise amino-terminal and/or carboxy-terminal fusion as well as intra-sequence insertion of single or multiple amino acids. Generally, insertions within the amino acid sequence are of the order of about 1 to 10 amino acids. Examples of amino- or carboxy-terminal fusions include fusion of the binding domain or activation domain of a transcriptional activator as used in the yeast two-hybrid system, phage coat proteins, (histidine)$_6$-tag, glutathione S-transferase-tag, protein A, maltose-binding protein, dihydrofolate reductase, Tag 100 epitope, c-myc epitope, FLAGa-epitope, lacZ, CMP (calmodulin-binding peptide), HA epitope, protein C epitope and VSV epitope.

Other derivatives of a CCS52 protein are "deletion variants", characterised by the removal of one or more amino acids from the protein.

Another derivative of a CCS52 protein is characterised by substitutions, and/or deletions and/or additions of naturally and non-naturally occurring amino acids compared to the amino acids of a naturally-occurring CCS52 protein. A derivative may also comprise one or more non-amino acid substituents compared to the amino acid sequence from which it is derived. Such non-amino acid substituents include for example, non-naturally occurring amino acids, a reporter molecule or other ligand, covalently or non-covalently bound to the amino acid sequence. Such a reporter molecule may be bound to facilitate the detection of the CCS52 protein.

Another variant of a CCS52 protein useful in the methods of the present invention is an active fragment of a CCS52 protein. "Active fragments" of a CCS52 protein encompass at least five contiguous amino acid residues of a CCS52 protein, which residues retain similar biological and/or functional activity to a naturally occurring protein or a part thereof. Suitable fragments include fragments of a CCS52 protein starting at the second or third or further internal methionine residues. These fragments originate from protein translation, starting at internal ATG codons, whilst retaining its functionality in the methods of the present invention. Suitable functional fragments of a CCS52 protein, or suitable portions of nucleic acids that correspond to such fragments, useful in the methods of the present invention, may have one or more of the conserved motifs of CCS52 proteins as represented by SEQ ID NO 7 to 16, whilst retaining its functionality in the methods of the present invention. One particular example of a functional fragment is a fragment of a rice CCS52 protein, for example of SEQ ID NO 6, which ends with the IR motif.

According to a preferred embodiment of the present invention, a method to improve plant growth characteristics comprises increased expression of a nucleic acid encoding a CCS52 protein. Methods for obtaining increased expression of genes or gene products (proteins) are well documented in the art and include, for example, overexpression driven by an operably linked promoter, or the use of transcription enhancers or translation enhancers. The term overexpression as used herein means any form of expression that is additional to the original wild-type expression level. Preferably the nucleic acid to be introduced into the plant and/or the nucleic acid that is to be overexpressed in the plant is in the sense direction with respect to the promoter to which it is operably linked. Preferably, in the methods of the present invention a nucleic acid encoding a CCS52 protein is overexpressed in a plant, such as a CCS52 nucleic acid of SEQ ID NO 1.

Alternatively and/or additionally, increased expression of a CCS52 gene or increased level, and/or activity of a CCS52 protein in a plant cell, may be achieved by mutagenesis. For example, the mutations may be responsible for altered control of an endogenous CCS52 gene, resulting in more expression of the gene, relative to the wild-type gene. Mutations can also cause conformational changes in a protein, resulting in higher levels and/or more activity of the CCS52 protein. Such mutations or such mutant genes may be selected, or isolated and/or introduced into the same or different plant species in order to obtain plants having improved growth characteristics. Examples of such mutants include dominant positive mutants of a CCS52 gene.

According to a further aspect of the present invention, there is provided genetic constructs and vectors to facilitate introduction and/or to facilitate expression and/or to facilitate maintenance in a host cell of the nucleic acids useful in the methods according to the invention. Therefore, according to a further embodiment of the present invention, there is provided a genetic construct comprising:

(a) a nucleic acid encoding a CCS52 protein or a variant thereof; operably linked to
(b) a medium-strength promoter, and optionally
(c) a transcription termination sequence.

Constructs useful in the methods according to the present invention may be constructed using recombinant DNA technology well known to persons skilled in the art. The gene constructs may be inserted into vectors, which may be commercially available, suitable for transforming into plants and suitable for maintenance and expression of the gene of interest in the transformed cells. Preferably, the genetic construct according to the present invention is a plant expression vector, suitable for introduction and/or maintenance and/or expression of a nucleic acid in a plant cell, tissue, organ or whole plant.

The nucleic acid according to (a) is advantageously any of the nucleic acids described hereinbefore. A preferred nucleic acid is a nucleic acid represented by SEQ ID NO 1, 3 or 5, or a variant thereof as hereinbefore defined, or is a nucleic acid encoding a protein as represented by SEQ ID NO 2, 4 or 6, or a variant thereof as hereinbefore defined.

With the term "promoter" it meant a transcription control sequence. The promoter of (b) is operable in a plant, most preferably the promoter is derived from a plant sequence.

The terms "transcription control sequence" or "promoter" are used interchangeably herein and are to be taken in a broad context to refer to regulatory nucleic acids capable of effecting expression of the sequences to which they are operably linked. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative, which confers, activates or enhances expression of a nucleic acid molecule in a cell, tissue or organ.

The term "operably linked" as used herein refers to a functional linkage between the promoter sequence and the gene of interest, such that the promoter sequence is able to initiate transcription of the gene of interest. Preferably, the gene of interest is operably linked in the sense orientation to the promoter.

The term "medium-strength promoter" means a promoter other than a strong promoter and refers to the expression level in green vegetative tissues.

Advantageously, any promoter may be used for the methods of the invention, provided that it has a medium-strength expression pattern in green vegetative tissues. These promoters have, when compared to a strong constitutive promoter (such as the strong constitutive/ubiquitous CaMV35S promoter), a lower expression level at least in green vegetative tissues. Promoters useful in the methods of the present invention do not reach the same strong expression level in green vegetative tissue of a plant as the CaMV35S promoter.

Preferably, the medium-strength promoter is of overall medium-strength during vegetative growth of the plant. One example of such a promoter is the sunflower ubiquitin promoter.

The term "medium-strength promoter" clearly does not include a CaMV35S promoter, which is known to be a very strong promoter. To the contrary, a medium-strength promoter has an expression level in green vegetative tissue that is at least 10-fold lower than the CaMV35S promoter. A person skilled in the art will recognize that for many plant species the CaMV35S promoter activity has been measured and that in many different plant species, such as rice and corn, the level of activity of the CaMV35S promoter is very high.

One method to measure the promoter strength is through the use of promoter-beta-glucuronidase fusions. The promoter if hereby fused to the *Escherichia coli* uidA gene encoding beta-glucuronidase and the chimeric construct is transformed into a plant. Proteins are extracted from the plant material and GUS activity is measured (Jefferson et al., 1987, EMBO J. 20; 6(13):3901-7). Promoter activity is then calculated as the optical density in units per mg of extracted protein.

Examples of measurements of CaMV35S expression levels have been described previously, for example for rice (Baftraw and Hall, 1990, Plant Mol. Biol. 15(4): 527-38), for tobacco (Jefferson et al., 1987, EMBO J., 20-6(13): 3901-7) and for *Arabidopsis* (S. Planchais, PhD. thesis University of Ghent, 2000).

In the context of this invention, GUS activity is measured from vegetative tissues after germination. Preferably, these measurements are performed during vegetative growth of the plant, for example after 2, preferably after 4 weeks post germination.

According to one embodiment of the present invention, the medium-strength promoter is a constitutive promoter. The term "constitutive" as defined herein refers to a promoter that is expressed substantially continuously and substantially in all tissues of a plant. Examples of useful constitutive promoters are ubiquitin promoters (in case of monocots intron-less ubiquitin promoters), such as rice or maize ubiquitin promoters.

According to one particular embodiment of invention, the medium-strength promoter is the sunflower ubiquitin promoter (without intron). The term "medium-strength promoter" as used herein therefore also means a promoter that has the same or similar activity, as the sunflower ubiquitin promoter in *Arabidopsis thaliana*. Similar activity in this context means an activity that is at most 20-fold higher or lower than the sunflower ubiquitin promoter, preferably at most 10-fold higher or lower or 5-fold higher or lower or 3-fold higher or lower.

Alternatively and according to another embodiment of the invention, the medium-strength promoter is a tissue-preferred promoter, characterized by the fact that it shows medium-strength expression in green vegetative tissue. The term "tissue-specific" promoter is used interchangeably herein with a "tissue-preferred" promoter. A promoter useful in the methods of the present invention may have a strong expression level, in other parts of the plant but the green vegetative tissue. For example, the *Arabidopsis thaliana* 2S2 promoter, which confers strong expression in seeds, may be used for the methods of the present invention. Besides the 2S2 promoter, other suitable tissue-preferred promoters include pPROLAMIN or pOLEOSIN, or promoters that show strong expression in aleurone, embryo, scutellum or endosperm. One example of a useful young-tissue preferred promoter is the beta-expansin promoter.

In document WO99/64451, it was suggested to clone a CCS52 gene under control of the endod12Ams promoter or the Srglb3 promoter in order to have a positive effect on differentiation and somatic embryogenesis. These positive effects have never been shown. These promoters are disclaimed from the constructs of the present invention.

Optionally, in the genetic construct according to the invention, one or more terminator sequences may also be incorporated. The term "transcription termination sequence" encompasses a control sequence at the end of a transcriptional unit, which signals 3' processing and polyadenylation of a primary transcript and termination of transcription. Additional regulatory elements, such as transcriptional or translational enhancers, may be incorporated in the genetic construct. Those skilled in the art will be aware of terminator and enhancer sequences, which may be suitable for use in performing the invention. Such sequences would be known or may readily be obtained by a person skilled in the art.

The genetic constructs of the invention may further include an origin of replication, which is required for maintenance and/or replication in a specific cell type. One example is when a genetic construct is required to be maintained in a bacterial cell as an episomal genetic element (e.g. plasmid or cosmid). Preferred origins of replication include, but are not limited to, the f1-ori and colE1.

The genetic construct may optionally comprise a selectable marker gene. As used herein, the term "selectable marker gene" includes any gene, which confers a phenotype on a cell in which it is expressed to facilitate the identification and/or selection of cells, which are transfected or transformed with a genetic construct of the invention. Suitable markers may be selected from markers that confer antibiotic or herbicide resistance. Cells containing the recombinant DNA will thus be able to survive in the presence of antibiotic or herbicide concentrations that kill untransformed cells. Examples of selectable marker genes include genes conferring resistance to antibiotics (such as nptII encoding neomycin phosphotransferase capable of phosphorylating neomycin and kanamycin, or hpt encoding hygromycin phosphotransferase capable of phosphorylating hygromycin), to herbicides (for example, bar which provides resistance to Basta; aroA or gox providing resistance against glyphosate), or genes that provide a metabolic trait (such as manA that allows plants to use mannose as sole carbon source). Visual marker genes result in the formation of colour (for example, beta-glucuronidase, GUS), luminescence (such as luciferase) or fluorescence (Green Fluorescent Protein, GFP, and derivatives thereof). Further examples of suitable selectable marker genes include the ampicillin resistance gene (Ampr), tetracycline resistance gene (Tcr), bacterial kanamycin resistance gene (Kanr), phosphinothricin resistance gene, and the chloramphenicol acetyltransferase (CAT) gene, amongst others.

According to a further embodiment of the present invention, there is provided a method for the production of transgenic plants having improved growth characteristics relative to corresponding wild-type plants, comprising:
(a) introducing into a plant cell a CCS52 nucleic acid or a variant thereof, preferably introducing a genetic construct as described hereinabove;
(b) cultivating said plant cell under conditions promoting plant growth.

"Introducing" the CCS52 nucleic acid or the genetic construct into the plant cell is preferably achieved by transformation. The term "transformation" as used herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention. The choice of tissue depends on the particular plant species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. Preferably, the CCS52 nucleic acid is stably integrated in the genome of the plant cell, which may be achieved, for example, by using a plant transformation vector or a plant expression vector having T-DNA borders, which flank the nucleic acid to be introduced into the genome.

Transformation of a plant species is now a fairly routine technique. Advantageously, any of several transformation methods may be used to introduce the gene of interest into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., 1882, Nature 296, 72-74; Negrutiu I. et al., June 1987, Plant Mol. Biol. 8, 363-373); electroporation of protoplasts (Shillito R. D. et al., 1985 Bio/Technol 3, 1099-1102); microinjection into plant material (Crossway A. et al., 1986, Mol. Gen. Genet. 202, 179-185); DNA or RNA-coated particle bombardment (Klein T. M. et al., 1987, Nature 327, 70) infection with (non-integrative) viruses and the like. A preferred method for the production of transgenic plants according to the invention, is an *Agrobacterium*-mediated transformation method.

Transgenic rice plants are preferably produced via *Agrobacterium*-mediated transformation using any of the well-known methods for rice transformation, such as the ones described in any of the following: published European patent application EP1198985, Aldemita and Hodges (Planta, 1996, 199: 612-617); Chan et al. (Plant Mol. Biol., 1993, 22 (3): 491-506); Hiei et al. (Plant J., 1994, 6 (2): 271-282); which disclosures are incorporated by reference herein as if fully set forth. In the case of corn transformation, the preferred method is as described in either Ishida et al. (Nat. Biotechnol., 1996, 14(6): 745-50) or Frame et al. (Plant Physiol., 2002, 129(1): 13-22), which disclosures are incorporated by reference herein as if fully set forth.

Generally after transformation, plant cells or cell groupings are selected for the presence of one or more markers, which are co-transformed with the CCS52 gene.

The resulting transformed plant cell, cell grouping, or plant tissue, may then be used to regenerate a whole transformed plant via regeneration techniques well known to persons skilled in the art. Therefore, cultivating the plant cell under conditions promoting plant growth, may encompass the steps of selecting and/or regenerating and/or growing to reach maturity.

Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The invention also includes host cells containing an isolated nucleic acid molecule encoding a CCS52 or a genetic construct as mentioned hereinbefore. Preferred host cells according to the invention are plant cells. Accordingly, there is provided plant cells, tissues, organs and whole plants that have been transformed with a genetic construct of the invention.

The present invention clearly extends to plants obtainable by any of the methods as described hereinbefore, which plants have improved growth characteristics relative to corresponding wild-type plants. The present invention extends to plants, which have increased expression levels of a nucleic acid encoding a CCS52 protein and/or increased level and/or activity od a CCS52 protein. The present invention extends to plants containing a genetic construct as described hereinabove, which plants have improved growth characteristics.

The present invention clearly also extends to any plant cell or plant produced by any of the methods described herein, and to all plant parts and propagules thereof. The present invention extends further to encompass the progeny of a primary transformed cell, tissue, organ or whole plant that has been produced by any of the aforementioned methods, the only requirement being that progeny exhibit the same genotypic and/or phenotypic characteristic(s) as those produced in the parent by the methods according to the invention.

The invention also extends to any part of the plant according to the invention, preferably a harvestable part of a plant, such as, but not limited to, a seed, leaf, fruit, flower, stem culture, stem, rhizome, root, tuber, bulb and cotton fiber.

The term "plant" as used herein encompasses whole plants, ancestors and progeny of the plants and plant parts, including seeds, shoots, stems, roots (including tubers), and plant cells, tissues and organs. The term "plant" also therefore encompasses suspension cultures, embryos, meristematic regions, callus tissue, leaves, seeds, roots, shoots, gametophytes, sporophytes, pollen, and microspores. Plants that are particularly useful in the methods of the invention include all plants which belong to the superfamily Viridiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnonrhiza*, *Burkea africana*, *Butea frondosa*, *Cadaba farinosa*, *Calimandra* spp, *Camellia sinensis*, *Canna indica*, *Capsicum* spp., *Cassia* spp., *Centroema pubescens*, *Chaenomeles* spp., *Cinnamomum cassia*, *Coffea arabica*, *Colophospenmum mopane*, *Coronillia varia*, *Cotoneaster serotina*, *Crataegus* spp., *Cucumis* spp., *Cupressus* spp., *Cyathea dealbata*, *Cydonia oblonga*, *Cryptomenia japonica*, *Cymbopogon* spp., *Cynthea dealbata*, *Cydonia oblonga*, *Dalbergia monetana*, *Davallia divaricata*, *Desmodium* spp., *Dicksonia squarosa*, *Diheteropogon amplectens*, *Dioclea* spp, *Dolichos* spp., *Dorycnium rectum*, *Echinochloa pyramidalis*, *Ehrartia* spp., *Eleusine coracana*, *Eragrestis* spp., *Erythrina* spp., *Eucalyptus* spp., *Euclea schimperi*, *Eulalia villosa*, *Fagopyrum* spp., *Feijoa sellowiana*, *Fragaria* spp., *Flemingia* spp, *Freycinetia banksii*, *Geranium thunbergii*, *Ginkgo biloba*, *Glycinejavanica*, *Gliricidia* spp, *Gossypium hirsutum*, *Grevillea* spp., *Guibourtia coleosperma*, *Hedysarum* spp., *Hemarthia altissima*, *Heteropogon contortus*, *Hordeum vulgare*, *Hyparrhenia rufa*, *Hypericum erectum*, *Hyperthelia dissolute*, *Indigo incamata*, *Iris* spp., *Leptarrhena pyrolifolia*, *Lespediza* spp., *Lettuca* spp., *Leucaena leucocephala*, *Loudetia simplex*, *Lotonus bainesii*, *Lotus* spp., *Macrotyloma axillare*, *Malus* spp., *Manihot esculenta*, *Medicago sativa*, *Metasequoia glyptostroboides*, *Musa sapientum*, *Nicotianum* spp., *Onobrychis* spp., *Ornithopus* spp., *Oryza* spp., *Peltophorum afncanum*, *Pennisetum* spp., *Persea gratissima*, *Petunia* spp., *Phaseolus* spp., *Phoenix canariensis*, *Phornium cookianum*, *Photinia* spp., *Picea glauca*, *Pinus* spp., *Pisum sativum*, *Podocarpus totara*, *Pogonarthria fleckii*, *Pogonarthria squarrosa*, *Populus* spp., *Prosopis cineraria*, *Pseudotsuga menziesii*, *Pterolobium stellatum*, *Pyrus communis*, *Quercus* spp., *Rhaphiolepis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys verticillata*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp, *Taxodium distichum*, *Themeda triandra*, *Trifolium* spp., *Triticum* spp., *Tsuga heterophylla*, *Vaccinium* spp., *Vicia* spp. *Vitis vinifera*, *Watsonia pyramidata*,

*Zantedeschia aethiopica, Zea mays*, amaranth, artichoke, asparagus, broccoli, brussel sprout, cabbage, canola, carrot, cauliflower, celery, collard greens, flax, kale, lentil, oilseed rape, okra, onion, potato, rice, soybean, straw, sugarbeet, sugar cane, sunflower, tomato, squash tea, trees, grasses (including forage grass) and algae, amongst others.

According to a preferred feature of the present invention, the plant is a crop plant, such as soybean, sunflower, canola, rapeseed, cotton, alfalfa, tomato, potato, tobacco, papaya, squash, poplar, eucalyptus, pine, leguminosa, flax, lupinus and sorghum. According to a further preferred embodiment of the present invention, the plant is a monocotyledonous plant, such as sugarcane, further preferably the plant is a cereal, such as rice, maize (including forage corn), wheat, barley, millet, oats and rye.

Accordingly, the present invention provides any of the methods as described hereinabove, or a transgenic plant as described hereinabove, wherein the plant is a monocotyledonous crop plant, preferably a cereal, more preferably wherein the plant is rice or corn.

According to a particular embodiment of the invention, the plant is a dicotyledonous crop plant, or a dicotyledonous ornamental, such as azalea.

Advantageously, performance of the method according to the present invention leads to plants having a variety of improved growth characteristics relative to corresponding wild-type plants.

The term "growth characteristic" as used herein, preferably refers to, but is not limited to, increased yield/biomass or to any other growth characteristic as described hereinafter.

The term "yield" refers to the amount of produced biological material and is used interchangeably with "biomass". For crop plants, "yield" also means the amount of harvested material per acre or unit of production. Yield may be defined in terms of quantity or quality. The harvested material may vary from crop to crop, for example, it may be seeds (e.g. for rice, sorghum or corn when grown for seed); above-ground biomass (e.g. for corn, when used as silage), roots (e.g. for sugar beet, turnip, potato), fruits (e.g. for tomato, papaya), cotton fibers, or any other part of the plant which is of economic value. "Yield" also encompasses yield stability of the plants. High yield stability means that yield is not strongly affected by changes in environmental conditions, such as suboptimal conditions caused by drought, chilling, freezing, heat, salinity or nutrient deficiency. "Yield" also encompasses yield potential, which is the maximum obtainable yield under optimal growth conditions. Yield may be dependent on a number of yield components, which may be monitored by certain parameters. These parameters are well known to persons skilled in the art and vary from crop to crop. For example, breeders are well aware of the specific yield components and the corresponding parameters for the crop they are aiming to improve. For example, key yield parameters for corn include number of plants per hectare or acre, number of ears per plant, number of rows (of seeds) per ear, number of kernels per row, and thousand kernel weight. For silage corn, typical parameters are the above-ground biomass and energy content. Key yield parameters for rice include number of plants per hectare or acre, number of panicles per plant, number of flowers (spikelets) per panicle, seed filling rate (number of filled seeds per spikelet) and thousand kernel weight.

Generally, the term "increased yield" means an increase in biomass in one or more parts of a plant relative to the biomass of corresponding reference plants, for example relative to corresponding wild-type plants. The plants of the present invention exhibit increased plant size, manifested in taller plants and increased rosette diameter. Accordingly, the term "yield/biomass" as used herein encompasses increased plant size.

The plants of the present invention also exhibit increased organ size, and therefore, the term "increased yield/biomass" as used herein encompasses increased organ size. For example, the plants according to the present invention are characterized by increased size of the leaves, which is particularly important for forage and feed crops (and ornamentals). Furthermore, the plants exhibit increased size of the stem. Besides the contribution to increased yield, for example, in trees, an increase in stem thickness contributes to improved wind/rain resistance, for example in cereals. Furthermore, the plants according to the invention exhibit increased seed size.

The plants of the present invention exhibit an increased number of organs, and therefore, the term "increased yield/biomass" as used herein encompasses increased number of organs. For example, the plants according to the present invention exhibit an increased number of the leaves, which is particularly important for forage crops and ornamentals. Furthermore, the plants according to the present invention exhibit an increased number of the branches (lateral branches, rosette branches), which contributes to increased bushiness of the plant. Also, the plants according to the invention have increased number of trichome branches. An increased biomass of specialised epidermal outgrowth structures is advantageous in the production of cotton fibres or glandular trichomes. Specialised trichomes may also be used for the production of useful metabolites, pharmaceutical compounds, nutraceuticals and food additives. Furthermore, the plants according to the invention exhibit increased number of flowers, which is important for ornamentals and seed crops.

Also encompassed within the term "increased yield/biomass" is increased seed yield. Seed-yield may be manifested by increased total seed weight, increased number of total seeds, increased number of filled seeds, and/or increased seed size. An increase in seed size and/or volume may also influence the composition of seeds.

The term "growth characteristic" as used herein, also encompasses plant architecture. For example, the plants of the invention exhibit altered leaf shape, which may be advantageous for ornamental plant, and altered vascularization, which is important for wood and/or paper and pulp producing trees. The term "architecture" as used herein encompasses the appearance or morphology of a plant, including any one or more structural features or combination of structural features thereof. Such structural features include the shape, size, number, position, texture, arrangement, and pattern of any cell, tissue or organ or groups of cells, tissues or organs of a plant, including the root, leaf, shoot, stem, petiole, trichome, flower, inflorescence (for monocots and dicots), panicles, petal, stigma, style, stamen, pollen, ovule, seed, embryo, endosperm, seed coat, aleurone, fibre, cambium, wood, heartwood, parenchyma, aerenchyma, sieve element, phloem or vascular tissue, amongst others. The term "architecture" therefore encompasses leaf area, leaf thickness, arrangement of lateral stems, stem shape and arrangement of flowers (and fruits).

The present invention also relates to use of a nucleic acid encoding a CCS52 protein or a variant thereof for improving plant growth characteristics, preferably for increasing yield, further preferably seed yield. Preferably, the nucleic acid is under the control of a medium-strength promoter.

Alternatively, increasing expression of a CCS52 nucleic acid, or introducing a CCS52 nucleic acid or the genetic construct into the plant cell, may be achieved by crossing or by breeding.

Furthermore, classical breeding techniques, aimed at improving plant growth characteristics, may be based on the selection of better performing allelic variants of a CCS52 gene, which better performing alleles may have an expression level that is higher than the wild-type level. Allelic variation may occur in nature, or may be created by mutagenic treatment of biological material, for example, by EMS mutagenesis. Therefore, the use of CCS52 allelic variants in breeding programmes, aimed at improving any of the growth characteristics as mentioned above, is also encompassed by the present invention; this may be in addition to their use in the methods according to the present invention. One example of a breeding program is a conventional marker-assisted breeding program.

Further information concerning the function of a CCS52 gene and related genes may be discovered by the use of reverse genetics, such a TILLING (Targeted Induced Local Lesions IN Genomes) in combination with the discovery of sites and motifs crucial for the gene and protein function (McCAllum et al., 2000, Plant Physiol 123(2):43942; Perry et al., 2003 Plant Physiol 131(3):866-71). Plants having mutant or dominant negative, or dominant positive phenotypes may be analysed and compared to identify the most effective mutations. Phenotypes may be compared with phenotypes identified in, for example, QTL (Quantitative Trait Loci) analysis and sequence information may be compared with the gene mapping included in a QTL. Both methods may be useful when combined in identifying new phenotypes of interest for crop breeding.

The present invention will now be described with reference to the following figures in which:

FIG. 1 is a map of the entry clone, p1627, containing the gene of interest, CCS52A1, (CDS0198) within the AttL1 and AttL2 sites for Gateway® cloning in the pDONR201 backbone. This vector also contains a bacterial kanamycin-resistance cassette and a bacterial origin of replication.

FIG. 2 is a map of the binary vector for expression in *Arabidopsis thaliana* of the *Arabidopsis thaliana* CCS52A1 gene (CDS0198) under the control of a sunflower ubiquitin promoter (pUBideltaT). The CCS52A1 expression cassette further comprises the T-zein and T-rbcS-deltaGA double terminator sequence. This expression cassette is located within the left border (LB repeat, LB Ti C58) and a right border (RB repeat, RB Ti C58) of the nopaline Ti plasmid. Cloned within these borders is also a selectable marker and a screenable marker, both under control of a constitutive promoter and followed by a nopaline (tNOS) or octopine (tOCS) transcription termination sequence. Furthermore, this vector also contains an origin of replication (pBR322 ori+bom) for bacterial replication and a bacterial selectable marker (Spe/SmeR) for bacterial selection.

FIG. 5 shows a first rosette leaf of a wild-type *Arabidopsis thaliana* plant (left) and of a transgenic *Arabidopsis thaliana* plant expressing a CCS52A1 gene under control of an ubiquitin promoter (right).

FIG. 6 shows leaf tissue of a wild-type *Arabidopsis thaliana* plant (left) and of a transgenic *Arabidopsis thaliana* plant expressing a CCS52A1 gene under control of an ubiquitin promoter.

FIG. 7 shows epidermis and trichomes of a wild-type *Arabidopsis thaliana* plant (A) and of a transgenic *Arabidopsis thaliana* plant expressing a CCS52A1 gene under control of an ubiquitin promoter (B).

FIG. 8 shows a wild-type *Arabidopsis thaliana* plant (left) and a transgenic Arabidposis thaliana plant expressing a CCS52A1 gene under the control of a 2S2 promoter (right), which are more bushier.

Figure 12:
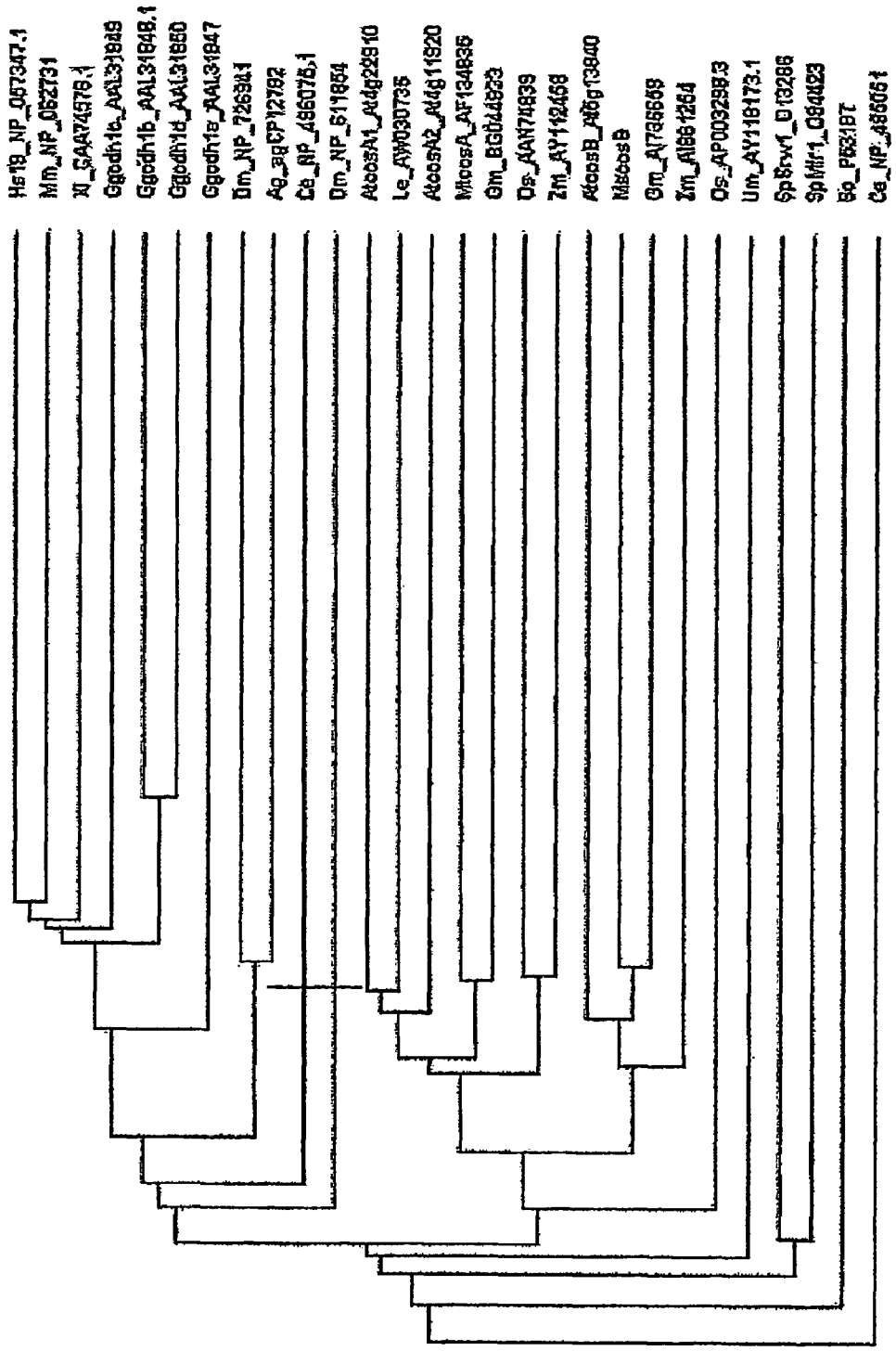

FIG. 12 shows a phylogentic tree of CCS52 related proteins in plants and animals. The sequences are presented by their Genbank accession number. Multiple sequence alignment across the entire sequences was done using CLUSTAL W (Higgins et al., (1994) Nucleic Acids Res. 22:4673-4680), with the BLOSSUM 62 matrix and with the parameters GAPOPEN 10, GAPEXT 0.05 and GAPDIST 8. The Phylogram view gives an estimate of phylogeny, i.e. branch lengths are proportional to evolutionary change.

FIG. 13 shows the conserved consensus motifs in plant CCS52 related proteins.

FIG. 14 shows the sequences of the present invention with their respective SEQ ID numbers.

Figure 15:
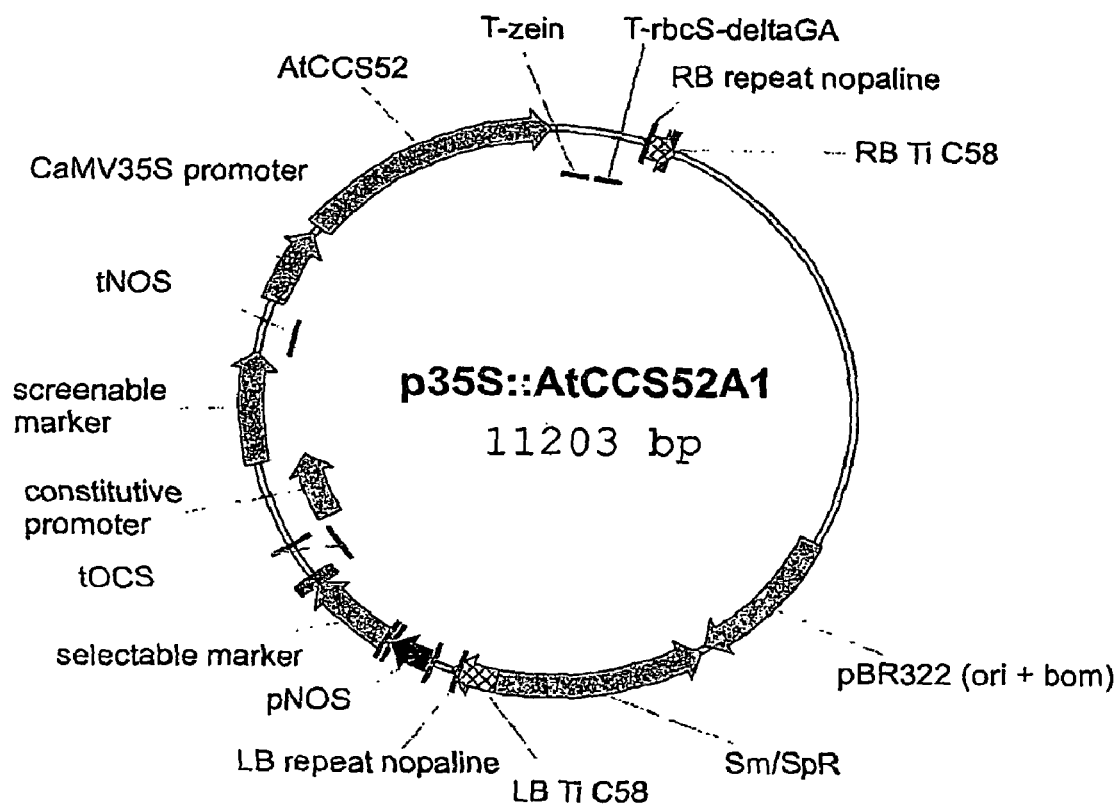

FIG. 15 is a map of the binary vector p35S::AtCCS52A1 for expression in *Arabidopsis thaliana* of the *Arabidopsis thaliana* CCS52A1 gene (internal reference CDS0198) under control of the CaMV35S promoter. The CCS52A1 expression cassette further comprises a T-zein and T-rbcS-deltaGA double transcription termination sequence. This expression cassette is located within the left border (LB repeat, LB Ti C58) and the right border (RB repeat, RB Ti C58) of the nopaline Ti plasmid. Within the T-DNA there is further provided a selectable and a screenable marker, both under control of a constitutive promoter and followed by a T-NOS or a T-OCS transcription terminator sequence. This vector further comprises an origin of replication (pBR322 ori+bom) for bacterial replication and a bacterial selectable marker (Spe/SmeR) for bacterial selection.

Figure 16:
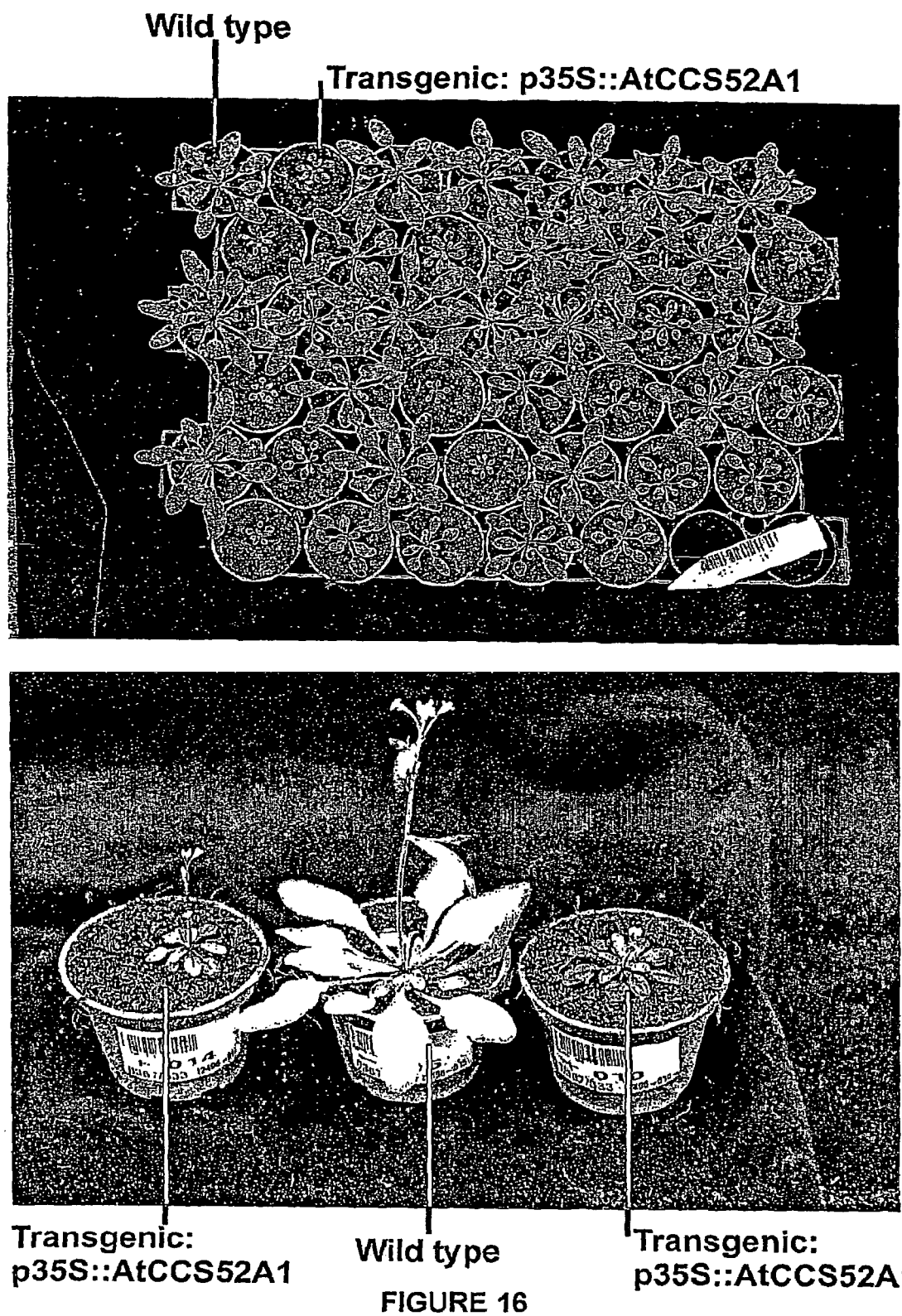

FIG. 16. shows wild-type *Arabidopsis thaliana* plants and transgenic *Arabidopsis thaliana* plants transformed with the vector carrying the p35S::AtCCS52A1 expression cassette.

Figure 17:
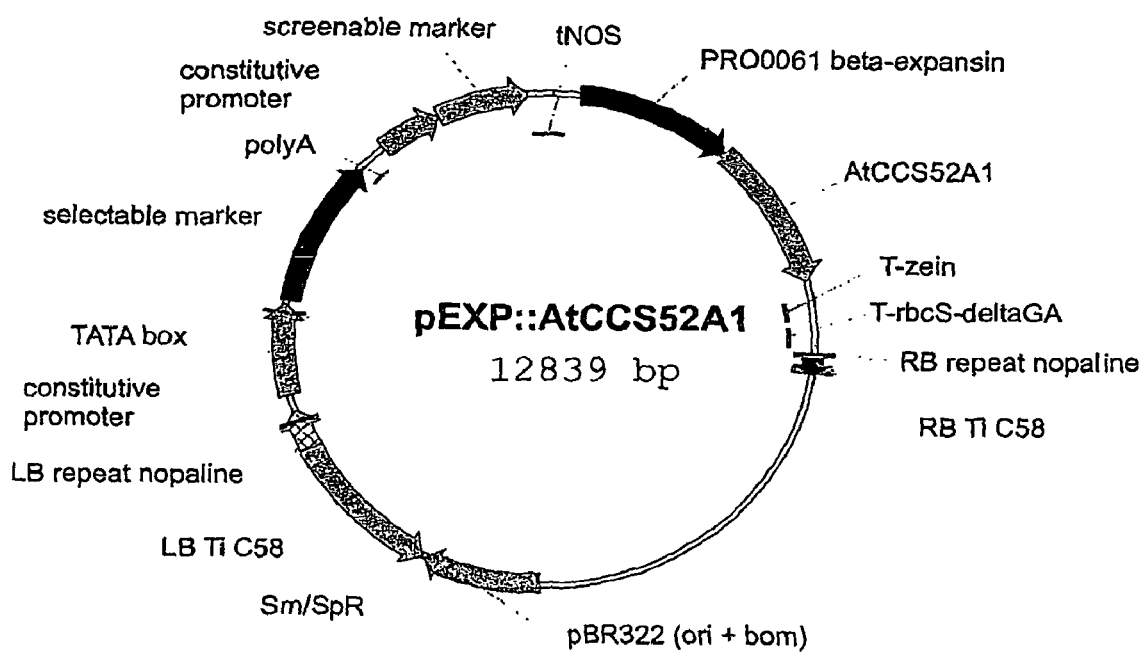

FIG. 17 is a map of the binary vector pEXP::AtCCS52A1 for expression in *Oryza sativa* of the *Arabidopsis thaliana* CCS52A1 gene (internal reference CDS0198) under the control of the rice beta-expansin promoter. The CCS52A1 expression cassette further comprises a T-zein and T-rbcS-deltaGA double transcription termination sequence. This expression cassette is located within the left border (LB repeat, LB Ti C58) and the right border (RB repeat, RB Ti C58) of the nopaline Ti plasmid. Within the T-DNA there is further provided a selectable and a screenable marker, both under control of a constitutive promoter and followed by polyA or a T-NOS transcription terminator sequence. This vector further comprises an origin of replication (pBR322 ori+bom) for bacterial replication and a bacterial selectable marker (Spe/SmeR) for bacterial selection.

EXAMPLES

The present invention will now be described with reference to the following examples, which are by way of illustration alone.

DNA Manipulation

Unless otherwise stated, recombinant DNA techniques are performed according to standard protocols described in Sambrook (2001) Molecular Cloning: a laboratory manual, 3rd Edition Cold Spring Harbor Laboratory Press, CSH, New York or in Volumes 1 and 2 of Ausubel et al. (1998), Current Protocols in Molecular Biology. Standard materials and methods for plant molecular work are described in Plant Molecular Biology Labfase (1993) by R.D.D. Croy, published by BIOS Scientific Publications Ltd (UK) and Blackwell Scientific Publications (UK).

Example 1

Cloning of *Arabidopsis thaliana* CCS52A1

Figure 1:
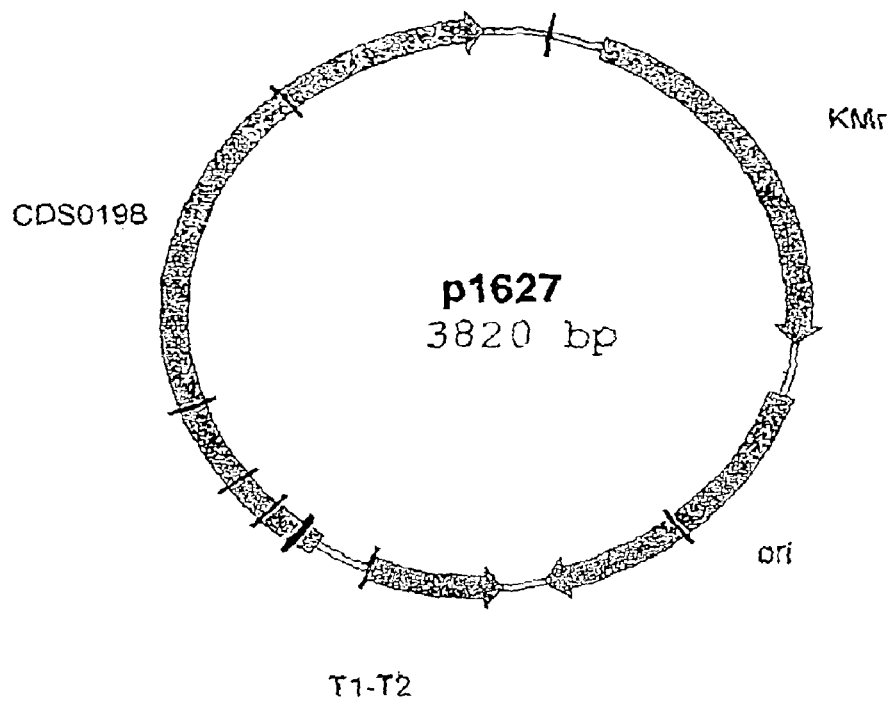

The *Arabidopsis* CCS52A1 gene (internal reference CDS0198) was amplified by PCR using as template an *Arabidopsis thaliana* seedling cDNA library (Invitrogen, Paisley, UK). After reverse transcription of RNA extracted from seedlings, the cDNA fragments were cloned into pCMV Sport 6.0. Average insert size of the cDNA library was 1.5 kb, and original number of clones was about $1.59 \times 10^7$ cfu. The original titer of $9.6 \times 10^5$ cfu/ml was brought to $6 \times 10^{11}$ cfu/ml after amplification of the library. After plasmid extraction of the clones, 200 ng of plasmid template was used in a 50 µl PCR mix. The primers used for PCR amplification, prm01391 with the sequence 5' GGGGACAAGTTTGTACAAAAAAG-CAGGCTTCACAATGGAAGAAGAAGATC CTACAGC 3' (SEQ ID NO 18) and prm01392 with the sequence 5' GGG-GACCACTTTGTACAAGAAAGCTGGGTTTCTCACC GAATTGTTGTTCTA C 3' (SEQ ID NO 19) an AttB site for Gateway recombination cloning (italics). PCR was performed using Hifi Taq DNA polymerase in standard conditions. A PCR fragment of the expected length was amplified and purified also using standard methods. The first step of the Gateway procedure, the BP reaction, was then performed, during which the PCR fragment recombines in vivo with the pDONR201 plasmid to produce the "entry clone", p1627 (FIG. 1). Plasmid pDONR201 was purchased from Invitrogen, as part of the Gateway® technology.

Example 2

Vector Construction (pUBI::AtCCS52A1)

Figure 2:
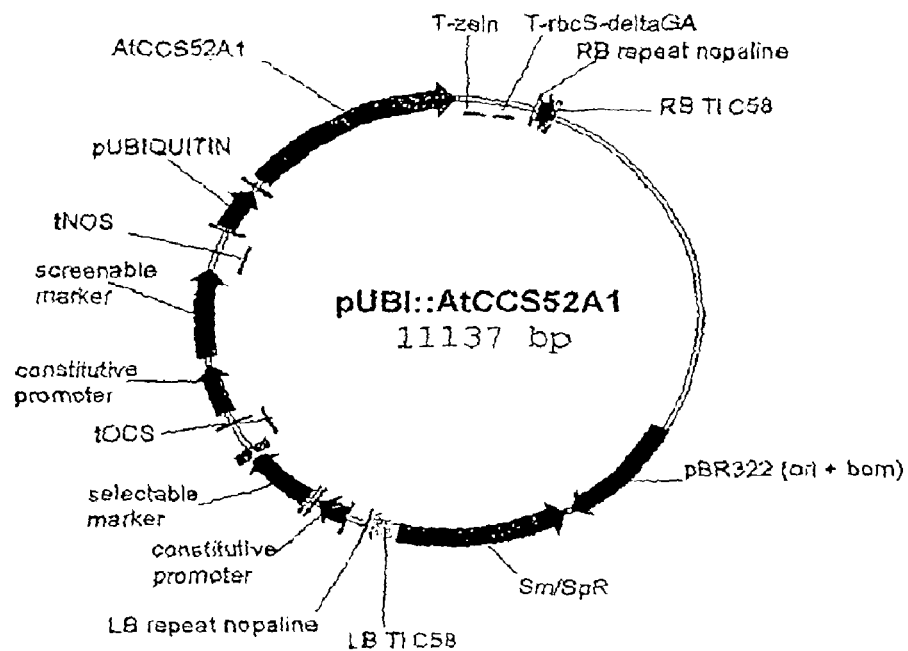

The entry clone p1627 was subsequently used in an LR reaction with p0712, a destination vector used for *Arabidopsis thaliana* transformation. This vector contains as functional elements within the T-DNA borders, a plant selectable marker, a screenable marker and a Gateway cassette intended for LR in vivo recombination with the sequence of interest already cloned in the entry clone. Upstream of this Gateway cassette lies the sunflower ubiquitin promoter (internal reference PRO155) for constitutive expression of the gene of interest. After the LR recombination step, the resulting expression vector pUBI::AtCCS52A1 (FIG. 2) was transformed into *Agrobacterium* strain LBA4044 and subsequently into *Arabidopsis thaliana* plants as described in Example 3.

Example 3

*Arabidopsis* Transformation

Sowing and Growing of Parental Plants

For the parental plants, approximately 12 mg of wild-type seeds from *Arabidopsis thaliana* (ecotype Columbia) was suspended in 27.5 ml of 0.2% agar solution. The seeds were incubated for 2 to 3 days at a temperature of 4° C. and were then sown. The seeds were then allowed to germinate under the following standard conditions: 22° C. during the day, 18° C. at night, 65-70% relative humidity, 12 hours of photoperiod, sub-irrigation with water for 15 min every 2 to 3 days. The developed seedlings were planted in pots of 5.5 cm diameter, containing a mixture of sand and peat (ratio 1:3). The plants were allowed to grow under the same standard conditions as mentioned above.

*Agrobacterium* Growth Conditions and Preparation

*Agrobacterium* strain C58C1R1F with helper plasmid pMP90 containing vector pUBI::AtCCS52A1 was inoculated in a 50 ml plastic tube containing 1 ml Luria Broth (LB) without antibiotics. The culture was shaken at 28° C. for 8-9 h. After addition of 10 ml of LB without antibiotic, the plastic tube was shaken overnight at 28° C. The OD at 600 nm was monitored. At an optical density of approximately 2.0, 40 ml of 10% sucrose and 0.05% Silwet L-77 (a chemical mixture of polyalkyleneoxide modified heptamethyltrisiloxane (84%) and allyloxypolyethyleneglycol methyl ether (16%), OSI Specialties Inc.) was added to the culture. The *Agrobacterium* culture obtained was labelled CD2175 and used to transform the parental *Arabidopsis* plants.

Flower Dip

When each parental plant had one inflorescence of 7-10 cm in height, the inflorescences were inverted into the *Agrobacterium* culture and agitated gently for 2-3 seconds. 2 plants per transformation were used. Subsequently, the plants were returned to normal growing conditions as described above.

Seed Collection 5 weeks after the flowers were dipped in the *Agrobacterium* culture, watering of the plants was stopped. The plants were incubated at 25° C. with a photoperiod of 20 hours. One week later, the seeds were harvested and placed in a seed drier for one week. The seeds were then cleaned and collected in 15 ml plastic tubes. The seeds were stored at 4° C. until further processing.

Example 4

Evaluation of Transformed *Arabidopsis* Plants

Selection of the First Generation of Transgenic Plants 100 mg of seeds were placed in a 50 ml plastic tube and suspended in 27 ml of a 0.2% agar solution. The tubes were stored at 4° C. for 3 days to release the seeds from dormancy. Following this period, the seed suspension was examined under blue light to determine the presence of transformed seeds. 20 bright fluorescent seeds (expressing the selectable marker) were aspirated with a Pasteur pipette, transferred to a 15 ml plastic tube, and the suspension volume was adjusted to 15 ml with a 0.2% agar solution. The same amount of non-fluorescent seed was transferred to a separate 15 ml plastic tube and the suspension volume adjusted to 15 ml with a 0.2% agar solution. The suspension of expressing seeds was evenly dispensed as drops of 50 µl on one half of a 50×30 cm tray containing a mixture of sand and soil in a ratio of 1 to 2. The non-expressing seeds were dispensed in the same way on the other half of the tray. The tray was placed in a greenhouse under the following conditions: 22° C. during the day, 18° C. at night, 60% relative humidity, 20 hour photoperiod, sub-irrigation once a day with water for 15 min. On the 14th day after sowing, 5 expressing and 5 non-expressing seedlings were transplanted into individual pots of 10 cm diameter filled with a mixture of sand and peat (ratio 1:3).

Cultivation and Imaging of the First Generation of Transgenic Plants

The pots were then placed in a greenhouse under the same conditions as described for the trays. The pots were sub-irrigated for 15 minutes, once a week, or more if needed. On the $21^{st}$, $28^{th}$, $35^{th}$, $42^{nd}$ and $49^{th}$ day after sowing, the rosettes of each plant were photographed using a digital camera. On the $35^{th}$, $42^{nd}$, $49^{th}$ and $56^{th}$ day after sowing, the inflorescence of each plant was photographed, using a digital camera. The number of pixels corresponding to plant tissues was recorded on each picture, converted to $cm^2$ and used as a measurement of plant size. On the $57^{th}$ day after sowing, when the first siliques were ripening, a breathable plastic bag was placed on each plant and tightly attached at the base of the plants to collect the shedding seeds. On the $90^{th}$ day after sowing, when all the siliques were ripe, the seeds were collected and placed in a seed drier for 1 week before storage in a sealed container at 4° C.

Seed Yield of the First Generation of Transgenic Plants

Harvested inflorescences of the T1 plants were taken and gently rubbed to release seeds from the siliques. The mixture of seeds and chaff was then passed over a mesh to remove large fragments of stems, leaves, siliques, etc. The seeds were then poured onto a vibrating gutter equipped with a vacuum cleaner allowing the lighter fragments, such as petals and small fibers, to be aspirated whilst retaining the heavier seeds. Data on the seed parameters were measured using an automated system.

A similar procedure was followed to evaluate the phenotypic characteristics of *Arabidopsis* T2 lines. At least 15 expressing and at least 15 non-expressing seedlings were transplanted into individual pots with a diameter of 10 cm (containing a mixture of sand and peat in a ratio of 1 to 3) and processed as described above. The phenotypic characteristics, as described above, were inherited to further generations.

Example 5

Phenotypic Characteristics of pUBI::AtCCS52A1 Transgenic Plants

Increased Biomass

CCS52 transgenic plants showed increased biomass relative to control plants. This was manifested by increased leaf size (see FIGS. 4, 5 and 6).

Figure 3:
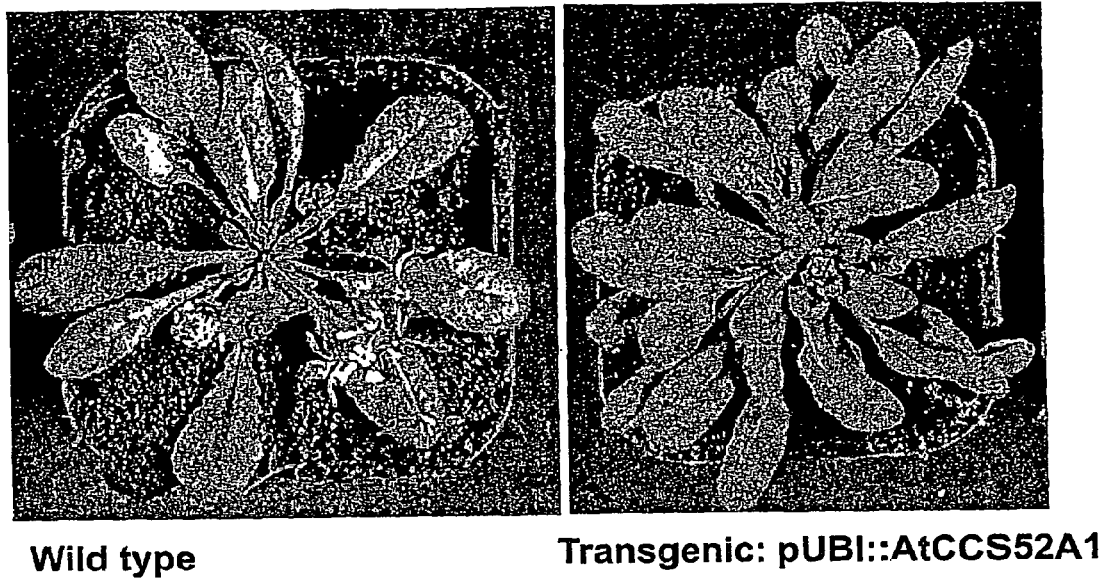
FIG. 3 shows an aerial view of a wild-type *Arabidopsis thaliana* plant (left) and a transgenic *Arabidopsis thaliana* plant expressing a CCS52A1 transgene under control of an ubiquitin promoter (right). Both plants are 4 weeks old.

Increased leaf biomass was also manifested by increased number of rosette leaves (see FIG. 3) and increased number of cauline leaves (FIG. 8).

Figure 9:
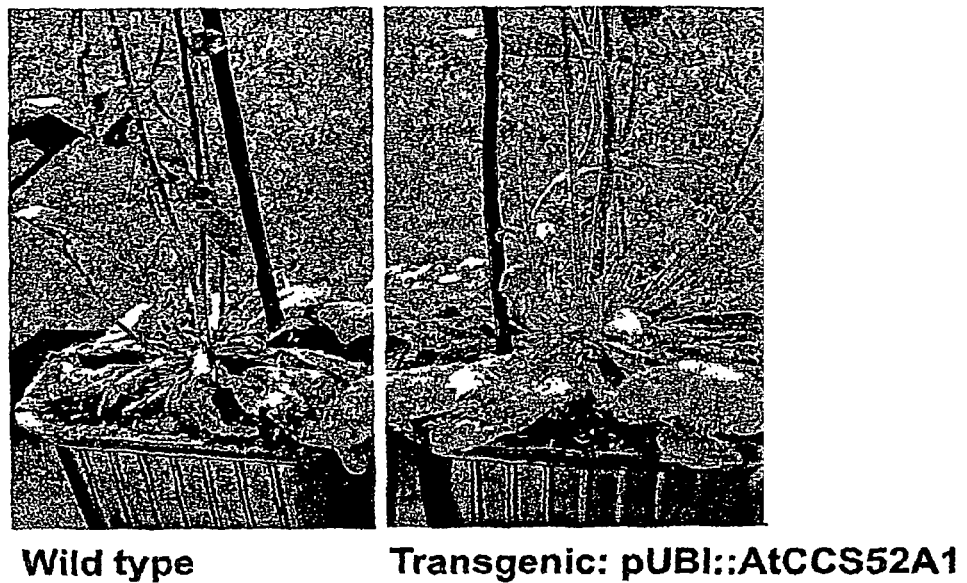
FIG. 9 shows a wild-type *Arabidopsis thaliana* plant (left) and a transgenic *Arabidposis thaliana* plant expressing a CCS52A1 gene under the control of an ubiquitin promoter (right).
Figure 10:
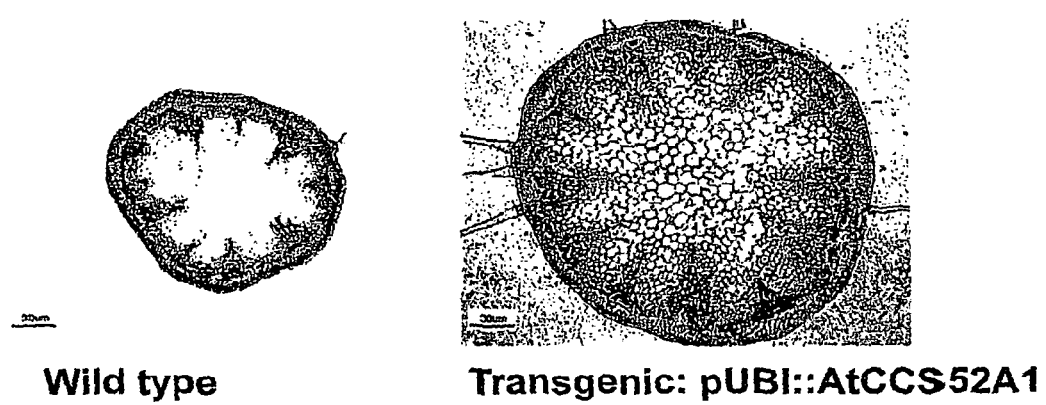
FIG. 10 shows transversal sections of the main stem of a wild-type *Arabidopsis thaliana* plant (left) and of a transgenic *Arabidopsis thaliana* plant expressing a CCS52A1 gene under control of an ubiquitin promoter (right).

Increased biomass was further manifested by increased stem thickness and more branching, which leads to a bushy phenotype. As illustrated in FIG. 9 and FIG. 10, pUBI::CCS52 transgenic plants have an increased rosette diameter as well as an increased (main) stem diameter and an increased diameter of the lateral branches. As a consequence it is estimated that overall plant biomass is multiplied by 3 to 4 in CCS52 transgenic *Arabidopsis* plants.

Modified Trichomes

As shown in FIG. 7, transgenic plants have trichomes with increased number of branches relative to the wild-type trichomes.

Modified Plant and Organ Shape

Figure 4:
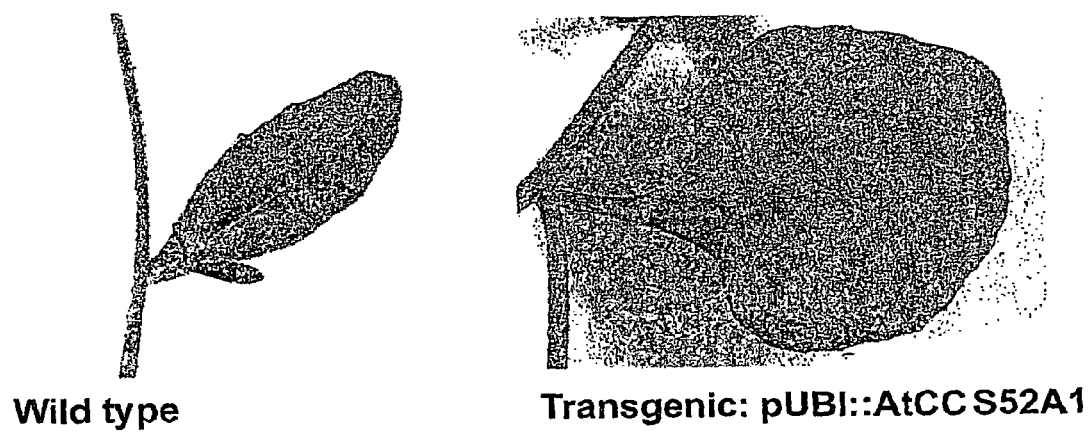
FIG. 4 shows a first cauline leaf of a Wild-type *Arabidopsis thaliana* plant (left) and of a transgenic *Arabidopsis thaliana* plant expressing a CCS52A1 gene under control of an ubiquitin promoter (right).

As shown in FIG. 4, the cauline leaf of the transgenic plant was of a different shape and of a larger size than the corresponding wild-type plant. As shown in FIG. 5, the rosette leaf of the transgenic plant had increased width and a larger area than the corresponding wild-type leaf. Further, this figure illustrates that a substantial increase of the vascularisation system was visible in the transgenic leaf.

Increase Yield—Seed Yield

Figure 11:
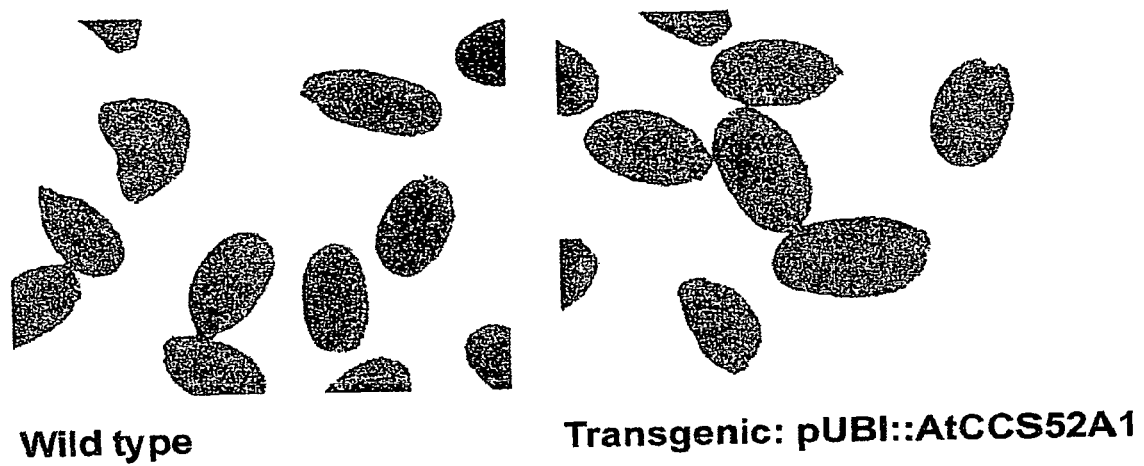
FIG. 11 shows seeds produced by a wild-type *Arabidopsis thaliana* plant (left) and by a transgenic *Arabidopsis thaliana* plant expressing a CCS52A1 gene under the control of an ubiquitin promoter (right).

As shown in FIG. 11, seed size was enlarged in the pUBI::CCS52 transgenic plant.

Example 6

Overexpression of AtCCS52A1 Under Control of the 2S2 Promoter Resulted in Bushier Plants Starting from the entry clone p1627, an expression vector was made in a similar way as described in Examples 1 and 2, except that the promoter upstream of the AtCCS52A1 gene was the *Arabidopsis* 2S2 seed-preferred promoter. This expression vector was transformed into *Arabidopsis* as described in Example 3 and plant evaluation was carried out as described in Example 4.

The phenotypic characteristics of the p2S2::CCS52 transformed plants was similar as the pUBI::CCS52 transformed plants described in Example 5. It was observed that p2S2::CCS52 transformed plants had increased biomass of leaves, increased number of branches and/or increased biomass of stems. As further illustrated in FIG. 8, the p2S2::CCS52 transgenic plant had an increased number of leaves, at least 2 times more rosette branches, thicker stems and more lateral branches, which gave rise to a bushier phenotype. Furthermore, these plants showed more flowers.

Example 7

Overexpression of CCS52 Under Control of the CaMV35S Promoter in *Arabidopsis* Resulted in Small, Aberrant Plants Starting from the entry clone p1627, an expression vector was made in a similar way as described in Examples 1 and 2, except that the promoter upstream of the AtCCS52A1 gene was the CaMV35S promoter. The resulting expression vector p35S::AtCCS52A1 (FIG. 15) was transformed into *Arabidopsis* as described in Example 3 and plant evaluation was carried out as described in Example 4.

*Arabidopsis* plants were regenerated and grown under optimal growth conditions as mentioned in Example 4. Nullizygote plant without the transgene were alternated with transgenic plant comprising the transgene in a growing tray (FIG. 16). During growth in optimal conditions, a significant difference between transgenic and wild-type plant was observed. After 5 to 6 weeks the plants were photographed (FIG. 16). At this stage the transgenic plants showed a small and aberrant phenotype compared with the mature and healthy wild-type plant. The transgenic plant clearly had smaller leaves, smaller or no stems, smaller rosette diameter, fewer leaves and fewer flowers compared to the wild-type plant. Clearly the p35S::CCS52 transgenic plants suffered from an early growth arrest. These transgenic plants are small and have aberrant organ formation. In transgenic plants the leaves were reddish, indicating that these plant suffered from stress and the aberrant plants produced significantly reduced amounts of siliques and seeds, compared to wild-type plants.

Example 8

Overexpression of AtCCS52 Under Control of Different Medium-Strength Promoters in Rice Starting from the entry clone p1627, different expression vectors are made in a similar way as described in Examples 1 and 2, except that the destination vector for the LR recombination reaction is a destination vector useful for transformation of *Oryza sativa*. This destination vector carries as functional elements within the T-DNA borders, a plant selectable marker, a screenable marker and a Gateway cassette intended for LR in vivo recombination with the CCS52 sequence already cloned in the entry clone. Different versions of this destination vector have different medium-strength promoters upstream of this Gateway cassette. The different resulting expression vectors therefore have different promoters upstream of the CCS52 gene.

One example of such an expression vector, pEXP::AtCCS52A1 carrying the rice beta-expansin promoter (PRO0061) upstream of the AtCCS52A1 gene, is represented in FIG. 17. Other examples of expression vectors are CD02376, carrying the rice prolamin promoter (PRO090); or CD05509, carrying the rice Oleosin 18 kDa promoter (PRO0218); or CD13390, carrying the rice putative protochlorophyllide reductase promoter (PRO0123), or a vector carrying the methallothionein promoter upstream of the AtCCS52A1 gene.

Similar vectors are made, for the expression of other CCS52A genes or CCS52B genes under control of the promoters as mentioned hereinabove.

All these expression vectors are suitable for the transformation of rice following the protocols as mentioned hereinabove.

AtCCS52A1 transgenic rice plants, overexpressing AtCCS52A1 under control of a medium-strength promoter, have improved growth characteristics. Especially, the transgenic rice plants have increased yield/biomass, manifested by increased plant size (increased plant area and/or increased plant height) or increased harvest index, which is the ratio of the total biomass over the harvested biomass. Increased biomass is also manifested by increased organ size such as increased leaf size, increased seed size (increased thousand kernel weight (TKW)), increased seed yield/seed biomass or increased stem diameter. Increased biomass is also manifested by increased number of organs such as increased number of leaves, increased number of branches, increased number of tillers, increased number of panicles, increased number of flowers, increased number of seeds or increased number of filled seeds or increased filling rate. Further these transgenic rice plants show early flowering (shorter life cycle), compared to the corresponding nullizygotes.

Example 9

Overexpression of CCS52 Under Control of a Medium-Strength Promoter in Corn

Similar constructs as described in Example 7 are made for the transformation of corn and the methods of the invention described herein are also used in corn (*Zea mays*). To this aim, a CCS52 gene, for example, a corn orthologue, is cloned under control of a promoter operable in corn, in a plant transformation vector suitable for *Agrobacterium*-mediated corn transformation. The promoter operable in corn may for example, be a medium-strength promoter, which is constitutive, for example, an ubiquitin promoter or any of the useful promoters as mentioned hereinabove. Methods to use for corn transformation have been described in literature (Ishida et al., Nat. Biotechnol. 1996 June; 14(6):745-50; Frame et al., Plant Physiol. 2002 May; 129(1):13-22).

Transgenic (inbred) lines made by these methods may be crossed with another non-transgenic or transgenic (inbred) line or be self/sib-pollinated. Importantly, transgenic (inbred) lines may be used as a female or male parent. Inheritability and copy number of the transgene are checked by quantitative real-time PCR and Southern blot analysis and expression levels of the transgene are determined by reverse PCR and Northern analysis. Transgenic events with single copy insertions of the transgene and with varying levels of transgene expression are selected for further evaluations in subsequent generations.

Progeny seeds obtained as described hereinabove are germinated and grown in the greenhouse in conditions well adapted for corn (16:8 photoperiod, 26-28° C. daytime temperature and 20-24° C. night time temperature) as well under water-deficient, nitrogen-deficient, and excess NaCl conditions. Null segregants from the same parental line (inbred line or hybrids), as well as wild-type plants of the same inbred line or hybrids are used as controls. The progeny plants are evaluated on different biomass and developmental parameters, including but not limited to plant height, stalk width, nodes below ear, nodes above ear, brace roots, number of leaves, leaf greenness, leaf angle, total above-ground area time to tassel, time to silk, time to maturity, ear height, ear number, ear length, ear weight, row number, kernel number, grain moisture. Kernel traits include but are not limited to kernel size, kernel weight, starch content, protein content, and oil content are also monitored. Corn yield is calculated according to well-known methods. Corn plants transformed with a CCS52 protein show improved growth characteristics. More particularly they show an improvement in any one or more of the abovementioned biomass and developmental parameters.

Transgenic events that are most significantly improved compared to corresponding control lines are selected for further field-testing and marker-assisted breeding, with the objective of transferring the field-validated transgenic traits into another germplasm. The phenotyping of maize for growth and yield-related parameters in the field is conducted using well-established protocols. The corn plants are particularly evaluated on yield components at different plant densities and under different environmental conditions. Subsequent improvements for introgressing specific loci (such as transgene containing loci) from one germplasm into another is also conducted using well-established protocols including but not limited to MAS.

Example 10

Overexpression of AtCCS52A2, AtCCS52B or Orthologues from Other Plants, Such as OsCCS52A The experiments as described in Examples 7 to 9 are repeated with other CCS52 genes.

The AtCCS52A2 (internal reference CDS0199) is cloned under control of the rice Oleosin 18 kDa promoter (PRO0128) in vector CD04769, the rice Prolamin promoter (PRO0090) in vector CD04778, the rice beta-expansin promoter (PRO0061) in vector CD13386 or the rice putative protochlorophyllide reductase promoter (PRO0123) in vector CD13522.

AtCCS52B (CDS0390) is cloned under control of the rice prolamin promoter (PRO0090) in the vector CD02164, the rice beta-expansin promoter (PRO0061) in vector CD13388 or the rice metallothionein promoter (PRO0126) in the vector CD13530.

Plants transformed with a CCS52 gene under the control of a medium-strength promoter, for example, transformed with one of the constructs as mentioned above, show improved growth characteristics, such as increased plant size, increased organ size and/or increased number of organs.

The invention claimed is:

1. A method for increasing plant yield or biomass, comprising
   1) introducing into a plant a nucleic acid encoding a CCS52 protein under the control of a tissue-specific promoter or a ubiquitin promoter, wherein said CCS52 protein comprises
      a) SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, and SEQ ID NO: 16; or
      b) SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 16, and SEQ ID NO: 15; and
   2) selecting a plant having increased yield or biomass as compared to a corresponding control plant.

2. The method of claim 1, wherein said increased yield or biomass comprises increased plant size, increased organ size or increased number of organs.

3. The method according to claim 2, wherein said increased organ size is selected from increased leaf size, increased seed size or increased stem diameter.

4. The method according to claim 2, wherein said increased number of organs is selected from increased number of leaves, increased number of branches, increased number of flowers or increased number of seeds.

5. The method according to claim 1, wherein said CCS52 protein is a CCS52A protein.

6. The method of claim 1, wherein said nucleic acid comprises SEQ ID NOs: 1, 3, or 5, or a nucleic acid encoding the protein of SEQ ID NOs: 2, 4, or 6.

7. The method according to claim 1, wherein the promoter is selected from the group consisting of an ubiquitin promoter, a metallothionein promoter, and a beta-expansin promoter.

8. A genetic construct comprising:
   (a) a CCS52 nucleic acid encoding a CCS52 protein; operably linked to
   (b) a tissue-specific promoter or a ubiquitin promoter; and optionally
   (c) a transcription termination sequence;
   wherein the genetic construct when expressed in a plant or plant cell results in increased yield or biomass as compared to a corresponding control plant or plant cell;
   wherein said CCS52 protein comprises
   1) SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, and SEQ ID NO: 16; or
   2) SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 16, and SEQ ID NO: 15.

9. The genetic construct of claim 8, wherein the promoter is selected from the group consisting of an ubiquitin promoter, a metallothionein promoter, and a beta-expansin promoter.

10. A method for the production of a transgenic plant having increased yield or biomass relative to a corresponding wild-type plant, comprising:
    a) introducing into a plant or plant cell the genetic construct of claim 8;
    b) cultivating said plant or plant cell under conditions promoting plant growth.

11. A host cell comprising the genetic construct of claim 8.

12. A plant obtained by the method of claim 1, which plant has increased yield or biomass relative to a corresponding wild-type plant.

13. A transgenic plant comprising the genetic construct of claim 8, which plant has increased yield or biomass relative to a corresponding wild-type plant.

14. The transgenic plant of claim 13, wherein said plant is a monocotyledonous plant.

15. The transgenic plant of claim 13, wherein said plant is a dicotyledoneous plant.

16. A plant part of the plant of claim 12, wherein the plant part comprises the nucleic acid.

17. A progeny of the plant of claim 12, wherein the progeny comprises the nucleic acid.

18. The method of claim 1, wherein the CCS52 protein comprises SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

19. The genetic construct of claim 8, wherein the CCS52 protein comprises SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

20. The method of claim 1, wherein the promoter is a tissue-specific promoter.

21. The method of claim 1, wherein the promoter comprises a metallothionein promoter.

22. The method of claim 1, wherein the promoter comprises a beta-expansin promoter.

23. The genetic construct of claim 8, wherein the promoter is a tissue-specific promoter.

24. The genetic construct of claim 8, wherein the promoter comprises a metallothionein promoter.

25. The genetic construct of claim 8, wherein the promoter comprises a beta-expansin promoter.

26. The method of claim 1, wherein the nucleic acid encodes a protein comprising a sequence having at least 95% sequence identity to the sequence of SEQ ID NO: 2, SEQ ID NO: 4, or SEQ ID NO: 6.

27. The genetic construct of claim 8, wherein the nucleic acid encodes a protein comprising a sequence having at least 95% sequence identity to the sequence of SEQ ID NO: 2, SEQ ID NO: 4, or SEQ ID NO: 6.

\* \* \* \* \*

SEQUENCE LISTING

```
<160> NUMBER OF SEQ ID NOS: 19

<210> SEQ ID NO 1
<211> LENGTH: 1905
<212> TYPE: DNA
<213> ORGANISM: Arabidopsis thaliana
<220> FEATURE:
<221> NAME/KEY: misc_feature
<223> OTHER INFORMATION: CCS52A1 cDNA

<400> SEQUENCE: 1
atggaagaag aagatcctac agcaagcaat gtgataacga attcgaattc ttcatctatg      60
agaaacctat cgccggcgat gaatactccg gtggtttcac ttgagtcacg aatcaatcga     120
ttaatcaatg ctaatcaatc tcaatcacca tcaccatcat cactatcaag gtctatatac     180
tctgatagat ttatccccag tagatccgga tccaatttcg ctcttttcga tctatctcct     240
tctcctagta aagatggtaa ggaagatgga gctggctctt acgctactct gttgcgtgcg     300
gcgatgtttg gtcctgagac gccggagaag agagatatta ctgggttttc ttcttccagg     360
aatattttta ggtttaagac ggagactcat cggtctttga attcgttttc tccttttggt     420
gttgatgatg attctcctgg tgtttctcat agtggtcctg ttaaagctcc caggaaagtg     480
ccgcgatcgc cgtataagat tcttgatctc gttgacttta gatctttggt ttcgataatg     540
catgaaacaa tttgtgatct ttgtgatgtt ttggtctctg agggtctaga atttgagtct     600
gaggtattgg atgcaccggc cttgcaagat gattttatc tgaatcttgt ggattggtct     660
gcacaaaatg ttctagcagt gggactaggg aactgtgtgt atttatggaa tgcttgtagc     720
agcaaggtta ctaagttatg tgatctcgga gctgaggata gtgtttgctc agtgggttgg     780
gcgttacgtg gaactcatct ggctgttgga actagtaccg ggaaagttca gatatgggat     840
gcgtcacgct gcaagagaac aagaacaatg gaaggtcatc gtctaagagt tggagccctg     900
gcatggggtt catcggttct gtcatctggt agcagagaca agagtattct tcagagagac     960
ataaggtgtc aagaagatca tgtcagtaaa ttggcaggtc ataaatctga ggtatgcgga    1020
ctcaagtggt cttatgacaa cagagagcta gcatctggtg gaaacgacaa taggcttttt    1080
gtatggaacc aacattcaac acaaccggtt ttgaaatata gtgaacacac tgcagctgtt    1140
aaagccattg cttggtctcc tcatgttcat gggcttcttg cttctggtgg tggtactgct    1200
gatagatgca tacgtttttg gaatacaacc acgaatactc atttaagttc catagatact    1260
tgcagtcagg tatgcaatct agcttggtct aagaacgtaa acgagcttgt tagcacacac    1320
ggatactctc agaaccaaat cattgtctgg aaatacccaa ccatgtccaa aattgctact    1380
ctaaccggtc acacataccg agtcttatac cttgcggttt cacccgatgg acagacgatt    1440
gtaacaggag caggagatga aaccttaagg ttctggaatg ttttcccttc cccaaaatct    1500
cagaacacgg atagtgaaat cgggtcgtct ttctttggta gaacaacaat tcggtgagaa    1560
gttactttca aaacacacag aaaaagtcat aaattcttga tttcttcagc agcagccagc    1620
ttgagttggt cgtctcaacc aacttttttc acacgggagc agagagtcat taaattcttt    1680
```

```
tacacacgga tgcaacaaga tctaacccct ttgatttaat cacgatcttt gggtttccat    1740
caagatgcac aacattttcc cccaaaattt tccaaagtgt atatctttat tcaattttc     1800 ttcatatatc aaaatatagt ttcttttgta tttatttact tacgaacaca acattttata    1860
aaataagccc atgataataa tgcaataatt cgttaccatt ctctt                    1905
```

<210> SEQ ID NO 2
<211> LENGTH: 518
<212> TYPE: PRT
<213> ORGANISM: Arabidopsis thaliana
<220> FEATURE:
<221> NAME/KEY: MISC_FEATURE
<223> OTHER INFORMATION: CCS52A1 protein

<400> SEQUENCE: 2

```
Met Glu Glu Glu Asp Pro Thr Ala Ser Asn Val Ile Thr Asn Ser Asn
1               5                   10                  15

Ser Ser Ser Met Arg Asn Leu Ser Pro Ala Met Asn Thr Pro Val Val
            20                  25                  30

Ser Leu Glu Ser Arg Ile Asn Arg Leu Ile Asn Ala Asn Gln Ser Gln
        35                  40                  45

Ser Pro Ser Pro Ser Ser Leu Ser Arg Ser Ile Tyr Ser Asp Arg Phe
    50                  55                  60

Ile Pro Ser Arg Ser Gly Ser Asn Phe Ala Leu Phe Asp Leu Ser Pro
65                  70                  75                  80

Ser Pro Ser Lys Asp Gly Lys Glu Asp Gly Ala Gly Ser Tyr Ala Thr
                85                  90                  95

Leu Leu Arg Ala Ala Met Phe Gly Pro Glu Thr Pro Glu Lys Arg Asp
            100                 105                 110

Ile Thr Gly Phe Ser Ser Ser Arg Asn Ile Phe Arg Phe Lys Thr Glu
        115                 120                 125

Thr His Arg Ser Leu Asn Ser Phe Ser Pro Phe Gly Val Asp Asp Asp
    130                 135                 140

Ser Pro Gly Val Ser His Ser Gly Pro Val Lys Ala Pro Arg Lys Val
145                 150                 155                 160

Pro Arg Ser Pro Tyr Lys Ile Leu Asp Leu Val Asp Phe Arg Ser Leu
                165                 170                 175

Val Ser Ile Met His Glu Thr Ile Cys Asp Leu Cys Asp Val Leu Val
            180                 185                 190

Ser Glu Gly Leu Glu Phe Glu Ser Glu Val Leu Asp Ala Pro Ala Leu
        195                 200                 205

Gln Asp Asp Phe Tyr Leu Asn Leu Val Asp Trp Ser Ala Gln Asn Val
    210                 215                 220

Leu Ala Val Gly Leu Gly Asn Cys Val Tyr Leu Trp Asn Ala Cys Ser
225                 230                 235                 240

Ser Lys Val Thr Lys Leu Cys Asp Leu Gly Ala Glu Asp Ser Val Cys
                245                 250                 255

Ser Val Gly Trp Ala Leu Arg Gly Thr His Leu Ala Val Gly Thr Ser
            260                 265                 270

Thr Gly Lys Val Gln Ile Trp Asp Ala Ser Arg Cys Lys Arg Thr Arg
        275                 280                 285

Thr Met Glu Gly His Arg Leu Arg Val Gly Ala Leu Ala Trp Gly Ser
    290                 295                 300

Ser Val Leu Ser Ser Gly Ser Arg Asp Lys Ser Ile Leu Gln Arg Asp
305                 310                 315                 320
```

```
Ile Arg Cys Gln Glu Asp His Val Ser Lys Leu Ala Gly His Lys Ser
            325                 330                 335

Glu Val Cys Gly Leu Lys Trp Ser Tyr Asp Asn Arg Glu Leu Ala Ser
            340                 345                 350

Gly Gly Asn Asp Asn Arg Leu Phe Val Trp Asn Gln His Ser Thr Gln
            355                 360                 365

Pro Val Leu Lys Tyr Ser Glu His Thr Ala Ala Val Lys Ala Ile Ala
            370                 375                 380

Trp Ser Pro His Val His Gly Leu Leu Ala Ser Gly Gly Gly Thr Ala
385                 390                 395                 400

Asp Arg Cys Ile Arg Phe Trp Asn Thr Thr Asn Thr His Leu Ser
            405                 410                 415

Ser Ile Asp Thr Cys Ser Gln Val Cys Asn Leu Ala Trp Ser Lys Asn
            420                 425                 430

Val Asn Glu Leu Val Ser Thr His Gly Tyr Ser Gln Asn Gln Ile Ile
            435                 440                 445

Val Trp Lys Tyr Pro Thr Met Ser Lys Ile Ala Thr Leu Thr Gly His
            450                 455                 460

Thr Tyr Arg Val Leu Tyr Leu Ala Val Ser Pro Asp Gly Gln Thr Ile
465                 470                 475                 480

Val Thr Gly Ala Gly Asp Glu Thr Leu Arg Phe Trp Asn Val Phe Pro
            485                 490                 495

Ser Pro Lys Ser Gln Asn Thr Asp Ser Glu Ile Gly Ser Ser Phe Phe
            500                 505                 510

Gly Arg Thr Thr Ile Arg
            515

<210> SEQ ID NO 3
<211> LENGTH: 2028
<212> TYPE: DNA
<213> ORGANISM: Oryza sativa
<220> FEATURE:
<221> NAME/KEY: misc_feature
<223> OTHER INFORMATION: CCS52A cDNA

<400> SEQUENCE: 3
atccccaaat ctctcgcccc cacccatgga tcaccaccac caccacctgc cgccgccgcc      60
gccgcggtcg ccgatggaga actccgcgtc ctccaagccg cccaccccgg cgtccacccc     120
gtcgtcgcgc ctcgccgccg cgccgtcctc ccgcgtctcc tccgcggcgc cgcaccctc     180 cccgtcctcc tccgcgccca cgccggcctc gcggacggtc tacagcgacc gcttcatccc     240
cagccgcgcc ggatccaacc tcgcgctctt cgacctcgcc ccgtcgccgt cccaccacga     300
cgccgccgcc gccgccgcct cccccggcgc cgccccccc tccggatcta ccccggcctc      360
gtcgccctac tgcgcgctcc tccgcgccgc gctcttcggc ccaccacgc cgaccgggt      420 ggcgtcgtcg cgtccgcgt gctcctcctc ctcctccgcc ggggcgtcgc ccgtgggctc     480
acccgccacc ggcaacatat tcaggttcaa ggcggaggtg ccccggaatg ctaagcgcgc     540 cctttctcc gacggggacg acgagggcgt gctcttcccc ggggtgttca cgacgagggg      600
cactggcccc aggaagatcc ctaggtcacc ttataaggtg ctggatgctc ccgcattgca     660
ggatgacttc tacctgaacc ttgtggattg gtcttcgcat aatatccttg cagttggatt     720
ggggaattgt gtctacttat ggaatgcatg cagcagcaag gtcaccaagc tatgtgattt     780
gggggtggat gacaatgtct gttcagtggg ttgggcacag cgtggcactc accttgctgt     840
agggacaaac caaggcaaag ttcaggtatg ggatgccact cgttgtaaga gaataagaac     900
```

```
catggaaagc catcggatgc gagtaggtgc tcttgcatgg aattcatcat tgctttcgtc    960
aggcagtcgt gacaagagca tccttcacca tgatatccgt gcccaggatg attatattag   1020
tagacttgct gggcataaat cggaggtctg tgggctcaag tggtcttatg ataaccgtca   1080
gcttgcatct ggtggtaatg acaacagact ttatgtatgg aatcaacact cggcgcaccc   1140
ggtactgaag tatactgagc atacagcagc tgtcaaagct attgcgtggt cacctcatct   1200
tcatgggctg cttgcatctg gtggaggaac tgcagataga tgcatacgat tttggaatac   1260
caccacgaat atgcacttaa attgcgtcga cacaggcagt caggtctgta atcttgtatg   1320
gtcaaagaat gttaatgagc ttgttagcac tcatggatat tctcaaaatc agataattgt   1380
ttggcgatac ccaacaatgt caaagctcgc acattgaca ggccatacat atagggtatt    1440
atatttagcc atctccccag atggacagac tatagtaact ggcgctggtg atgaaacgct   1500
tcggttttgg aacgtgtttc catctcccaa gtcccagagt tctgacagcc taagtagcat   1560
cggggccaca tcatttgtta ggagctacat ccggtgacac tgagatgtgg taatctaata   1620
acacttggct cataagtcat aacactactg cagcagagtg ttgatgatca tcaatatcat   1680
tccatttgta ccacttgcat caccagttca tgaaccatca aacctagcca aattttagag   1740
atagtaggat gcagaatggt gaaactggct cgcagacctc ggagtggctc atttgctgaa   1800
tgctgtatat atttattcat tggctttgta ggagcgaaga tggcaaacac tgaccatccg   1860
caatgtacca ttgataagtt cacggcctcc tgttttttgtt tttgctgagt caacttggag   1920
ctggagctct tatgtatacc atgctagggc ttaacaacat tggccaactc atgatgctca   1980
ttgcatccaa gttggaatat gctaaggaag ctggagaatt tctggtgc                2028
```

<210> SEQ ID NO 4
<211> LENGTH: 507
<212> TYPE: PRT
<213> ORGANISM: Oryza sativa
<220> FEATURE:
<221> NAME/KEY: MISC_FEATURE
<223> OTHER INFORMATION: CCS52A protein

<400> SEQUENCE: 4

```
Met Glu Asn Ser Ala Ser Ser Lys Pro Pro Thr Pro Ala Ser Thr Pro
1               5                   10                  15

Ser Ser Arg Leu Ala Ala Ala Pro Ser Ser Arg Val Ser Ser Ala Ala
            20                  25                  30

Pro His Pro Ser Pro Ser Ser Ala Pro Thr Pro Ala Ser Arg Thr
        35                  40                  45

Val Tyr Ser Asp Arg Phe Ile Pro Ser Arg Ala Gly Ser Asn Leu Ala
    50                  55                  60

Leu Phe Asp Leu Ala Pro Ser Pro Ser His His Asp Ala Ala Ala Ala
65                  70                  75                  80

Ala Ala Ser Pro Gly Ala Pro Pro Ser Gly Ser Thr Pro Ala Ser
            85                  90                  95

Ser Pro Tyr Cys Ala Leu Leu Arg Ala Ala Leu Phe Gly Pro Thr Thr
            100                 105                 110

Pro Asp Arg Val Ala Ser Ser Ala Ser Ala Cys Ser Ser Ser Ser Ser
        115                 120                 125

Ala Gly Ala Ser Pro Val Gly Ser Pro Ala Thr Gly Asn Ile Phe Arg
    130                 135                 140

Phe Lys Ala Glu Val Pro Arg Asn Ala Lys Arg Ala Leu Phe Ser Asp
145                 150                 155                 160

Gly Asp Asp Glu Gly Val Leu Phe Pro Gly Val Phe Thr Thr Arg Gly
```

|     |     |     |     | 165 |     |     |     | 170 |     |     |     | 175 |     |
|-----|-----|-----|-----|-----|-----|-----|-----|-----|-----|-----|-----|-----|-----|

Thr Gly Pro Arg Lys Ile Pro Arg Ser Pro Tyr Lys Val Leu Asp Ala
                    180                    185                190

Pro Ala Leu Gln Asp Asp Phe Tyr Leu Asn Leu Val Asp Trp Ser Ser
          195                    200                205

His Asn Ile Leu Ala Val Gly Leu Gly Asn Cys Val Tyr Leu Trp Asn
210                    215                    220

Ala Cys Ser Ser Lys Val Thr Lys Leu Cys Asp Leu Gly Val Asp Asp
225                    230                235              240

Asn Val Cys Ser Val Gly Trp Ala Gln Arg Gly Thr His Leu Ala Val
                  245                  250              255

Gly Thr Asn Gln Gly Lys Val Gln Val Trp Asp Ala Thr Arg Cys Lys
          260                    265                270

Arg Ile Arg Thr Met Glu Ser His Arg Met Arg Val Gly Ala Leu Ala
          275                    280                285

Trp Asn Ser Ser Leu Leu Ser Ser Gly Ser Arg Asp Lys Ser Ile Leu
          290                    295                300

His His Asp Ile Arg Ala Gln Asp Asp Tyr Ile Ser Arg Leu Ala Gly
305                    310                315              320

His Lys Ser Glu Val Cys Gly Leu Lys Trp Ser Tyr Asp Asn Arg Gln
                  325                330              335

Leu Ala Ser Gly Gly Asn Asp Asn Arg Leu Tyr Val Trp Asn Gln His
                  340                345              350

Ser Ala His Pro Val Leu Lys Tyr Thr Glu His Thr Ala Ala Val Lys
          355                    360                365

Ala Ile Ala Trp Ser Pro His Leu His Gly Leu Leu Ala Ser Gly Gly
          370                    375              380

Gly Thr Ala Asp Arg Cys Ile Arg Phe Trp Asn Thr Thr Thr Asn Met
385                    390                395              400

His Leu Asn Cys Val Asp Thr Gly Ser Gln Val Cys Asn Leu Val Trp
                  405                410              415

Ser Lys Asn Val Asn Glu Leu Val Ser Thr His Gly Tyr Ser Gln Asn
          420                    425              430

Gln Ile Ile Val Trp Arg Tyr Pro Thr Met Ser Lys Leu Ala Thr Leu
          435                    440              445

Thr Gly His Thr Tyr Arg Val Leu Tyr Leu Ala Ile Ser Pro Asp Gly
          450                    455              460

Gln Thr Ile Val Thr Gly Ala Gly Asp Glu Thr Leu Arg Phe Trp Asn
465                    470                475              480

Val Phe Pro Ser Pro Lys Ser Gln Ser Ser Asp Ser Leu Ser Ser Ile
                  485                490              495

Gly Ala Thr Ser Phe Val Arg Ser Tyr Ile Arg
          500                    505

<210> SEQ ID NO 5
<211> LENGTH: 1587
<212> TYPE: DNA
<213> ORGANISM: Oryza sativa
<220> FEATURE:
<221> NAME/KEY: misc_feature
<223> OTHER INFORMATION: DNA encoding CCS52B protein

<400> SEQUENCE: 5
atgctaatgg gccggcccgc atggcagaga gagtacaacg gctactcggg tgggggccc    60 acagtcagag ggagacagct cgtgctagaa aaagtaggcg acttgcccac tccaaccaaa   120

```
gtgaccgttg caacctcatc tccgctcctc ttcctcctcc tcgtcgtcgt tgtcgtcgtc    180
ggcggcgcat ccagcctcga cgtgccggcg gcgccggcgc cgccgcgcct caacgtgccg    240
ccggcgatgg cggggggggct ccgcctcgat cccgccgtcg cctccccggc ccgcctcctc    300
ctcgacgtcc ccaagacgcc atccccttcc aagaccacgt acagcgaccg cttcatcccc    360
tgccgctcct cctcccgcct ccacaacttc gccctcctcg accgcgaccg cgcctccccc    420
tcctccacca ccgacgacgc cccctactcc cgcctcctcc gcgccgagat cttcggcccg    480
gactccccct cccggctcc ctcctccccc aacaccaacc tcttccgctt caagaccgac    540
cacccctcgc ccaaatcgcc cttcgccgcc tccgccgccg ccaccgccgg ccactacgac    600
tgcaccgccg gctccgctga atcctccacg ccgcgcaagc cgcccaggaa ggtccccaag    660
accccgcaca aggtcctgga cgcgccgtcg ctgcaggacg acttctacct caatcttgtc    720
gactggtcgt cgcagaacac gctcgccgtc ggcctcggga attgcgtcta cctctggtcg    780
gcttccaatt gcaaggtcac caagctctgc gatttggggc cagggacag cgtctgcgct    840
gtgcactgga cccgagaagg ctcctatctt gccatcggca ccagccttgg cgatgtccag    900
atttgggata gctctcgctg taaacggatt aggaacatgg gaggacacca aacacggact    960
ggtgtattag catggagctc ccgaatcttg tcctccggta gcagggacaa gaacatattg   1020
cagcatgaca tccgtgtccc aagtgactat atcagcaagt tctcagggca gatcagag    1080
aaccatgtat gtgcatcaag tgacagtttt tttggtcagg tctgtggact gaaatggtcg   1140
cacgacgacc gtgagcttgc atccggtgga aatgataatc agctgctagt atggaaccaa   1200
cgttcgcagc agccgatatt gaggctgaca gaacacacag ctgcagttaa agcaatagca   1260
tggtcaccac atcagcaagg cctcctggca tcaggtggtg gaaccgctga taggtgtatc   1320
aggttctgga acacggttaa tggaaacatg ctgaattcag tggacacagg cagccaggcg   1380
acttgtgagc actcatgggt attcccaaaa ccaaatcatg gtgtggaagt acccatctat   1440
gtcaaaggtt gctactctaa ctggacacac gctgcgagtg ctttaccttg caatgtcacc   1500
acaatagtaa caggagccgg ggatgaaacc ctcagatttt ggaatatttt tccttcaatg   1560
aagacacagg taggcatcta ttgttga                                       1587
```

<210> SEQ ID NO 6
<211> LENGTH: 528
<212> TYPE: PRT
<213> ORGANISM: Oryza sativa
<220> FEATURE:
<221> NAME/KEY: MISC_FEATURE
<223> OTHER INFORMATION: CCS52B protein

<400> SEQUENCE: 6

Met Leu Met Gly Arg Pro Ala Trp Gln Arg Glu Tyr Asn Gly Tyr Ser
1               5                   10                  15

Gly Gly Gly Pro Thr Val Arg Gly Arg Gln Leu Val Leu Glu Lys Val
            20                  25                  30

Gly Asp Leu Pro Thr Pro Thr Lys Val Thr Val Ala Thr Ser Ser Pro
        35                  40                  45

Leu Leu Phe Leu Leu Leu Val Val Val Val Val Gly Gly Ala Ser
    50                  55                  60

Ser Leu Asp Val Pro Ala Ala Pro Ala Pro Arg Leu Asn Val Pro
65                  70                  75                  80

Pro Ala Met Ala Gly Gly Leu Arg Leu Asp Pro Ala Val Ala Ser Pro
                85                  90                  95

Ala Arg Leu Leu Leu Asp Val Pro Lys Thr Pro Ser Pro Ser Lys Thr

-continued

```
                   100             105             110
Thr Tyr Ser Asp Arg Phe Ile Pro Cys Arg Ser Ser Arg Leu His
            115             120             125
Asn Phe Ala Leu Leu Asp Arg Asp Arg Ala Ser Pro Ser Ser Thr Thr
        130             135             140
Asp Asp Ala Pro Tyr Ser Arg Leu Leu Arg Ala Glu Ile Phe Gly Pro
145             150             155             160
Asp Ser Pro Ser Pro Ala Pro Ser Ser Pro Asn Thr Asn Leu Phe Arg
            165             170             175
Phe Lys Thr Asp His Pro Ser Pro Lys Ser Pro Phe Ala Ala Ser Ala
            180             185             190
Ala Ala Thr Ala Gly His Tyr Asp Cys Thr Ala Gly Ser Ala Glu Ser
            195             200             205
Ser Thr Pro Arg Lys Pro Pro Arg Lys Val Pro Lys Thr Pro His Lys
            210             215             220
Val Leu Asp Ala Pro Ser Leu Gln Asp Asp Phe Tyr Leu Asn Leu Val
225             230             235             240
Asp Trp Ser Ser Gln Asn Thr Leu Ala Val Gly Leu Gly Asn Cys Val
            245             250             255
Tyr Leu Trp Ser Ala Ser Asn Cys Lys Val Thr Lys Leu Cys Asp Leu
            260             265             270
Gly Pro Arg Asp Ser Val Cys Ala Val His Trp Thr Arg Glu Gly Ser
            275             280             285
Tyr Leu Ala Ile Gly Thr Ser Leu Gly Asp Val Gln Ile Trp Asp Ser
            290             295             300
Ser Arg Cys Lys Arg Ile Arg Asn Met Gly Gly His Gln Thr Arg Thr
305             310             315             320
Gly Val Leu Ala Trp Ser Ser Arg Ile Leu Ser Ser Gly Ser Arg Asp
            325             330             335
Lys Asn Ile Leu Gln His Asp Ile Arg Val Pro Ser Asp Tyr Ile Ser
            340             345             350
Lys Phe Ser Gly His Arg Ser Glu Asn His Val Cys Ala Ser Ser Asp
            355             360             365
Ser Phe Phe Gly Gln Val Cys Gly Leu Lys Trp Ser His Asp Asp Arg
            370             375             380
Glu Leu Ala Ser Gly Gly Asn Asp Asn Gln Leu Leu Val Trp Asn Gln
385             390             395             400
Arg Ser Gln Gln Pro Ile Leu Arg Leu Thr Glu His Thr Ala Ala Val
            405             410             415
Lys Ala Ile Ala Trp Ser Pro His Gln Gln Gly Leu Leu Ala Ser Gly
            420             425             430
Gly Gly Thr Ala Asp Arg Cys Ile Arg Phe Trp Asn Thr Val Asn Gly
            435             440             445
Asn Met Leu Asn Ser Val Asp Thr Gly Ser Gln Ala Thr Cys Glu His
            450             455             460
Ser Trp Val Phe Pro Lys Pro Asn His Gly Val Glu Val Pro Ile Tyr
465             470             475             480
Val Lys Gly Cys Tyr Ser Asn Trp Thr His Ala Ala Ser Ala Leu Pro
            485             490             495
Cys Asn Val Thr Thr Ile Val Thr Gly Ala Gly Asp Glu Thr Leu Arg
            500             505             510
Phe Trp Asn Ile Phe Pro Ser Met Lys Thr Gln Val Gly Ile Tyr Cys
            515             520             525
```

```
<210> SEQ ID NO 7
<211> LENGTH: 9
<212> TYPE: PRT
<213> ORGANISM: Artificial Sequence
<220> FEATURE:
<223> OTHER INFORMATION: consensus motif 1 of CCS52 protein
<220> FEATURE:
<221> NAME/KEY: MISC_FEATURE
<222> LOCATION: (1)..(6)
<223> OTHER INFORMATION: Xaa = unknown

<400> SEQUENCE: 7

Xaa Ser Xaa Xaa Xaa Xaa Phe Asp Leu
1               5

<210> SEQ ID NO 8
<211> LENGTH: 17
<212> TYPE: PRT
<213> ORGANISM: Artificial Sequence
<220> FEATURE:
<223> OTHER INFORMATION: consensus motif 2 of CCS52 protein
<220> FEATURE:
<221> NAME/KEY: MISC_FEATURE
<222> LOCATION: (1)..(15)
<223> OTHER INFORMATION: Xaa = unknwon

<400> SEQUENCE: 8

Xaa Xaa Xaa Xaa Xaa Xaa Tyr Xaa Xaa Leu Leu Xaa Xaa Xaa Xaa Phe
1               5                   10                  15

Gly

<210> SEQ ID NO 9
<211> LENGTH: 18
<212> TYPE: PRT
<213> ORGANISM: Artificial Sequence
<220> FEATURE:
<223> OTHER INFORMATION: consensus motif 3 of CCS52 protein
<220> FEATURE:
<221> NAME/KEY: MISC_FEATURE
<222> LOCATION: (13)..(14)
<223> OTHER INFORMATION: Xaa = unknown or absent
<220> FEATURE:
<221> NAME/KEY: MISC_FEATURE
<222> LOCATION: (1)..(12)
<223> OTHER INFORMATION: Xaa = unknown
<220> FEATURE:
<221> NAME/KEY: MISC_FEATURE
<222> LOCATION: (17)..(18)
<223> OTHER INFORMATION: Xaa = unknown

<400> SEQUENCE: 9

Xaa Xaa Xaa Xaa Asn Xaa Xaa Arg Phe Lys Xaa Xaa Xaa Xaa Arg Arg
1               5                   10                  15

Xaa Xaa

<210> SEQ ID NO 10
<211> LENGTH: 6
<212> TYPE: PRT
<213> ORGANISM: Artificial Sequence
<220> FEATURE:
<223> OTHER INFORMATION: consensus motif 4 of CCS52 protein

<400> SEQUENCE: 10

Ser Lys Val Thr Lys Leu
1               5

<210> SEQ ID NO 11
<211> LENGTH: 11
<212> TYPE: PRT
```

<213> ORGANISM: Artificial Sequence
<220> FEATURE:
<223> OTHER INFORMATION: consensus motif 5 of CCS52 protein
<220> FEATURE:
<221> NAME/KEY: MISC_FEATURE
<222> LOCATION: (2)..(7)
<223> OTHER INFORMATION: Xaa = unknown

<400> SEQUENCE: 11

Asp Xaa Xaa Ser Xaa Leu Xaa Gly His Lys Ser
1               5                   10

<210> SEQ ID NO 12
<211> LENGTH: 12
<212> TYPE: PRT
<213> ORGANISM: Artificial Sequence
<220> FEATURE:
<223> OTHER INFORMATION: consensus motif 6 of CCS52 protein
<220> FEATURE:
<221> NAME/KEY: MISC_FEATURE
<222> LOCATION: (3)..(10)
<223> OTHER INFORMATION: Xaa = unknown

<400> SEQUENCE: 12

His Ser Xaa Xaa Pro Xaa Leu Xaa Xaa Xaa Glu His
1               5                   10

<210> SEQ ID NO 13
<211> LENGTH: 14
<212> TYPE: PRT
<213> ORGANISM: Artificial Sequence
<220> FEATURE:
<223> OTHER INFORMATION: consensus motif 7 of CCS52 protein
<220> FEATURE:
<221> NAME/KEY: MISC_FEATURE
<222> LOCATION: (5)..(12)
<223> OTHER INFORMATION: Xaa = unknown

<400> SEQUENCE: 13

Trp Asn Thr Thr Xaa Xaa Xaa Xaa Leu Xaa Xaa Xaa Asp Thr
1               5                   10

<210> SEQ ID NO 14
<211> LENGTH: 14
<212> TYPE: PRT
<213> ORGANISM: Artificial Sequence
<220> FEATURE:
<223> OTHER INFORMATION: consensus motif 8 of CCS52 protein
<220> FEATURE:
<221> NAME/KEY: MISC_FEATURE
<222> LOCATION: (5)..(5)
<223> OTHER INFORMATION: Xaa = unknown

<400> SEQUENCE: 14

Leu Tyr Leu Ala Xaa Ser Pro Asp Gly Gln Thr Ile Val Thr
1               5                   10

<210> SEQ ID NO 15
<211> LENGTH: 13
<212> TYPE: PRT
<213> ORGANISM: Artificial Sequence
<220> FEATURE:
<223> OTHER INFORMATION: consensus motif 9 of CCS52 protein
<220> FEATURE:
<221> NAME/KEY: MISC_FEATURE
<222> LOCATION: (1)..(11)
<223> OTHER INFORMATION: Xaa = unknown

<400> SEQUENCE: 15

Xaa Xaa Gly Xaa Xaa Xaa Xaa Xaa Xaa Xaa Xaa Ile Arg
1               5                   10

<210> SEQ ID NO 16
<211> LENGTH: 7
<212> TYPE: PRT
<213> ORGANISM: Artificial Sequence
<220> FEATURE:
<223> OTHER INFORMATION: consensus C box
<220> FEATURE:
<221> NAME/KEY: MISC_FEATURE
<222> LOCATION: (6)..(6)
<223> OTHER INFORMATION: Xaa = unknown

<400> SEQUENCE: 16

Asp Arg Phe Ile Pro Xaa Arg
1               5

<210> SEQ ID NO 17
<211> LENGTH: 9
<212> TYPE: PRT
<213> ORGANISM: Artificial Sequence
<220> FEATURE:
<223> OTHER INFORMATION: consensus motif 1 of CCS52A proteins
<220> FEATURE:
<221> NAME/KEY: MISC_FEATURE
<222> LOCATION: (4)..(4)
<223> OTHER INFORMATION: Xaa = F or L
<220> FEATURE:
<221> NAME/KEY: MISC_FEATURE
<222> LOCATION: (9)..(9)
<223> OTHER INFORMATION: Xaa = L or I

<400> SEQUENCE: 17

Gly Ser Asn Xaa Ala Leu Phe Asp Xaa
1               5

<210> SEQ ID NO 18
<211> LENGTH: 57
<212> TYPE: DNA
<213> ORGANISM: Artificial Sequence
<220> FEATURE:
<223> OTHER INFORMATION: primer

<400> SEQUENCE: 18
ggggacaagt ttgtacaaaa aagcaggctt cacaatggaa gaagaagatc ctacagc        57

<210> SEQ ID NO 19
<211> LENGTH: 52
<212> TYPE: DNA
<213> ORGANISM: Artificial Sequence
<220> FEATURE:
<223> OTHER INFORMATION: primer

<400> SEQUENCE: 19
ggggaccact ttgtacaaga aagctgggtt tctcaccgaa ttgttgttct ac             52